United States Patent
Henderson

(10) Patent No.: US 10,111,663 B2
(45) Date of Patent: Oct. 30, 2018

(54) IMPLANT RETRIEVAL DEVICE

(75) Inventor: Jennifer Lake Henderson, Sunnyvale, CA (US)

(73) Assignee: Ancora Heart, Inc., Santa Clara, CA (US)

(*) Notice: Subject to any disclaimer, the term of this patent is extended or adjusted under 35 U.S.C. 154(b) by 399 days.

(21) Appl. No.: 14/000,167

(22) PCT Filed: Feb. 17, 2012

(86) PCT No.: PCT/US2012/025748
§ 371 (c)(1),
(2), (4) Date: Jan. 31, 2014

(87) PCT Pub. No.: WO2012/161769
PCT Pub. Date: Nov. 29, 2012

(65) Prior Publication Data
US 2014/0135799 A1    May 15, 2014

Related U.S. Application Data

(60) Provisional application No. 61/444,652, filed on Feb. 18, 2011, provisional application No. 61/537,017, filed on Sep. 20, 2011.

(51) Int. Cl.
*A61B 17/10* (2006.01)
*A61B 17/076* (2006.01)
(Continued)

(52) U.S. Cl.
CPC .......... *A61B 17/076* (2013.01); *A61B 17/221* (2013.01); *A61B 2017/00358* (2013.01); *A61B 2017/2212* (2013.01)

(58) Field of Classification Search
CPC ................ A61B 17/076; A61B 17/221; A61B 17/32056; A61B 2017/00358;
(Continued)

(56) References Cited

U.S. PATENT DOCUMENTS 3,181,533 A * 5/1965 Heath .................... A61B 17/26
606/113
3,656,185 A   4/1972 Carpentier
(Continued)

FOREIGN PATENT DOCUMENTS

WO    WO-95/15715 A1    6/1995
WO    WO-96/39942 A1    12/1996
(Continued)

OTHER PUBLICATIONS

International Search Report, dated Aug. 3, 2012, for PCT Patent Application No. PCT/US2012/25748, filed on Feb. 17, 2012, 2 pages.
(Continued)

*Primary Examiner* — Katrina Stransky
*Assistant Examiner* — Kankindi Rwego
(74) *Attorney, Agent, or Firm* — Cooley LLP

(57) ABSTRACT

Devices and methods are disclosed for retrieving an implant or tissue anchor during the course of a percutaneous medical procedure. An implant is provided having a retrieval tether attached to it. The retrieval tether is attached to the implant on one end, and the proximal end of the tether can be threaded through an implant retrieval device. The retrieval device comprises an inner elongate body that is used to capture and secure the retrieval tether. The retrieval device also comprises an outer elongate body that may be configured to be advanced over the retrieval tether from a location remote from the implant (e.g., outside a patient's body) to contact and retrieve the implant after it has been deployed and/or implanted within a patient's body.

19 Claims, 16 Drawing Sheets

(51) Int. Cl.
*A61B 17/221* (2006.01)
*A61B 17/00* (2006.01)

(58) Field of Classification Search
CPC .... A61B 2017/2212; A61B 2017/2217; A61B 17/072; A61B 17/08; A61B 17/083; A61B 17/10; A61B 17/128; A61B 17/1285; A61B 17/22031; A61B 17/24; A61B 2017/00353; A61B 2017/00362; A61B 2017/0411; A61B 2017/086; A61B 2017/22035; A61B 2018/1407; A61B 2018/141

USPC ............................................................ 606/113
See application file for complete search history.

(56) References Cited

U.S. PATENT DOCUMENTS

| | | | |
|---|---|---|---|
| 4,042,979 A | 8/1977 | Angell | |
| 4,290,151 A | 9/1981 | Massana | |
| 4,489,446 A | 12/1984 | Reed | |
| 5,016,640 A * | 5/1991 | Ruiz | A61M 25/0041 600/435 |
| 5,064,431 A | 11/1991 | Gilbertson et al. | |
| 5,324,298 A | 6/1994 | Phillips et al. | |
| 5,387,219 A | 2/1995 | Rappe | |
| 5,417,684 A * | 5/1995 | Jackson et al. | 606/1 |
| 5,527,323 A | 6/1996 | Jervis et al. | |
| 5,562,678 A | 10/1996 | Booker | |
| 5,571,215 A | 11/1996 | Sterman et al. | |
| 5,718,725 A | 2/1998 | Sterman et al. | |
| 5,735,290 A | 4/1998 | Sterman et al. | |
| 5,817,107 A | 10/1998 | Schaller | |
| 5,879,295 A * | 3/1999 | Li | A61B 18/1492 600/373 |
| 5,961,440 A | 10/1999 | Schweich, Jr. et al. | |
| 5,964,771 A | 10/1999 | Beyar et al. | |
| 6,050,936 A | 4/2000 | Schweich, Jr. et al. | |
| 6,059,715 A | 5/2000 | Schweich, Jr. et al. | |
| 6,125,852 A | 10/2000 | Stevens et al. | |
| 6,162,168 A | 12/2000 | Schweich, Jr. et al. | |
| 6,447,530 B1 | 9/2002 | Ostrovsky et al. | |
| 6,517,550 B1 | 2/2003 | Konya et al. | |
| 6,517,551 B1 * | 2/2003 | Driskill | A61B 17/22031 606/113 |
| 6,589,160 B2 | 7/2003 | Schweich, Jr. et al. | |
| 6,702,826 B2 | 3/2004 | Liddicoat et al. | |
| 6,718,985 B2 | 4/2004 | Hlavka et al. | |
| 6,723,038 B1 | 4/2004 | Schroeder et al. | |
| 6,793,618 B2 | 9/2004 | Schweich, Jr. et al. | |
| 6,908,424 B2 | 6/2005 | Mortier et al. | |
| 6,986,775 B2 | 1/2006 | Morales et al. | |
| 7,125,421 B2 | 10/2006 | Tremulis et al. | |
| 7,166,127 B2 | 1/2007 | Spence et al. | |
| 7,189,199 B2 | 3/2007 | McCarthy et al. | |
| 7,326,231 B2 | 2/2008 | Phillips et al. | |
| 7,452,325 B2 | 11/2008 | Schaller | |
| 7,479,155 B2 * | 1/2009 | Gainor et al. | 606/213 |
| 7,547,310 B2 * | 6/2009 | Whitfield | A61B 17/221 606/114 |
| 7,618,449 B2 | 11/2009 | Tremulis et al. | |
| 2002/0095175 A1 | 7/2002 | Brock et al. | |
| 2003/0032979 A1 | 2/2003 | Mortier et al. | |
| 2003/0233105 A1 | 12/2003 | Gayton | |
| 2004/0138693 A1 * | 7/2004 | Eskuri | A61F 2/013 606/200 |
| 2005/0070951 A1 | 3/2005 | Paganon | |
| 2005/0137689 A1 | 6/2005 | Salahieh et al. | |
| 2006/0173468 A1 | 8/2006 | Simmon et al. | |
| 2006/0190030 A1 | 8/2006 | To et al. | |
| 2006/0195008 A1 | 8/2006 | Whalen et al. | |
| 2007/0073337 A1 * | 3/2007 | Abbott et al. | 606/213 |
| 2007/0112422 A1 | 5/2007 | Dehdashtian | |
| 2007/0162048 A1 * | 7/2007 | Quinn | A61B 17/12122 606/113 |
| 2007/0250070 A1 * | 10/2007 | Nobis et al. | 606/113 |
| 2008/0208075 A1 * | 8/2008 | Goldenberg | 600/562 |
| 2008/0294177 A1 | 11/2008 | To et al. | |
| 2009/0182417 A1 | 7/2009 | Tremulis et al. | |
| 2009/0276038 A1 | 11/2009 | Tremulis et al. | |
| 2010/0076548 A1 | 3/2010 | Konno | |
| 2010/0198192 A1 | 8/2010 | Serina et al. | |
| 2010/0198208 A1 * | 8/2010 | Napp et al. | 606/27 |
| 2010/0222802 A1 * | 9/2010 | Gillespie et al. | 606/192 |

FOREIGN PATENT DOCUMENTS

| | | |
|---|---|---|
| WO | WO-97/27799 A1 | 8/1997 |
| WO | WO-97/27807 A1 | 8/1997 |
| WO | WO-03/105667 A2 | 12/2003 |
| WO | WO-03/105667 A3 | 12/2003 |
| WO | WO-2008/028135 A2 | 3/2008 |
| WO | WO-2008/028135 A3 | 3/2008 |
| WO | WO-2012/161769 A1 | 11/2012 |

OTHER PUBLICATIONS

Written Opinion dated Aug. 3, 2012, for PCT Patent Application No. PCT/US2012/25748, filed on Feb. 17, 2012, 5 pages.
Extended European Search Report dated Oct. 16, 2017, for EP Application No. 12 789 114.1, filed on Feb. 17, 2012, 6 pages.

\* cited by examiner

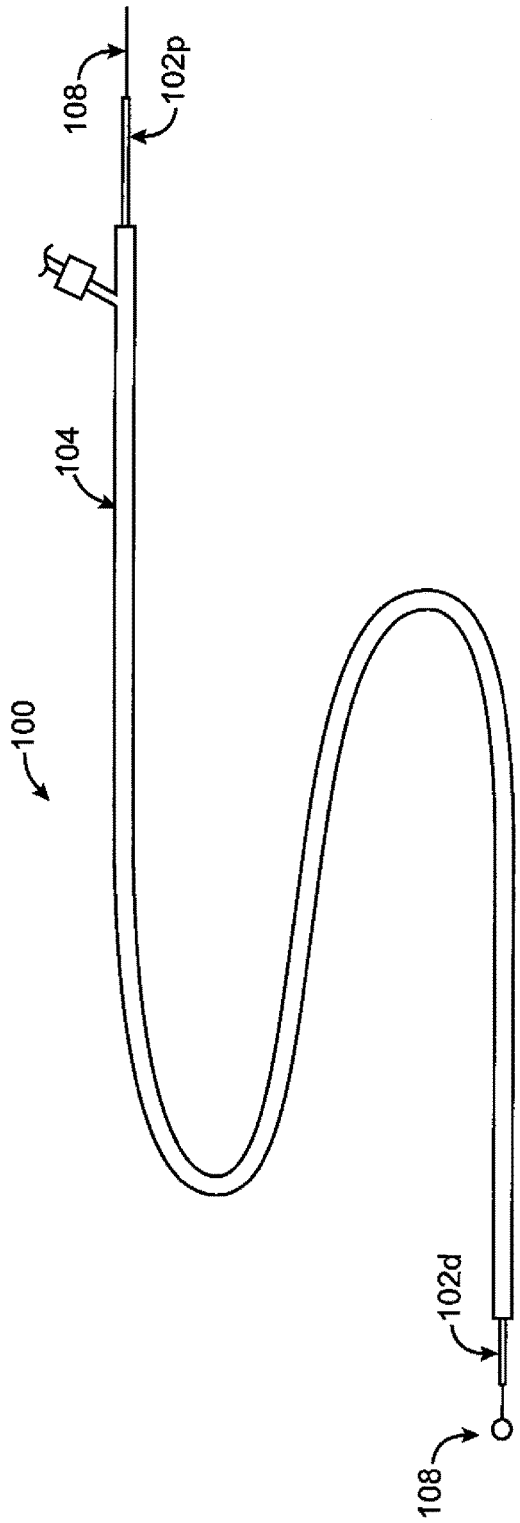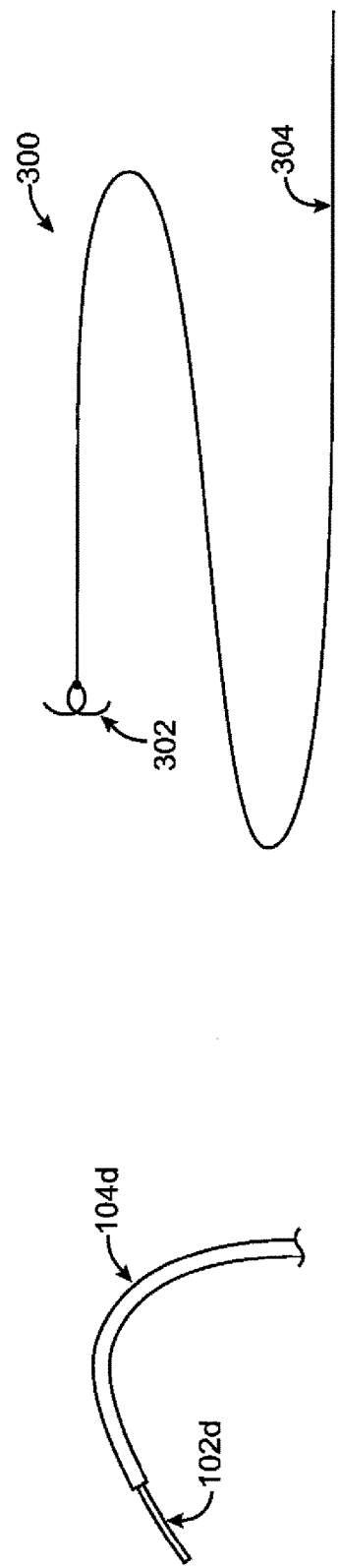

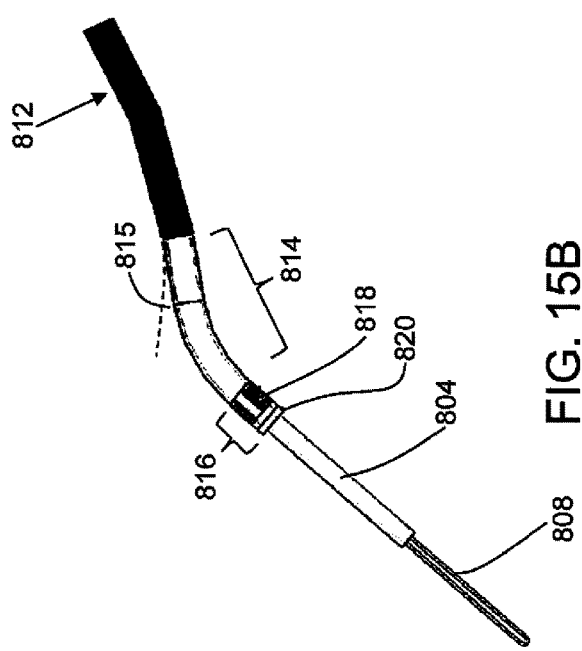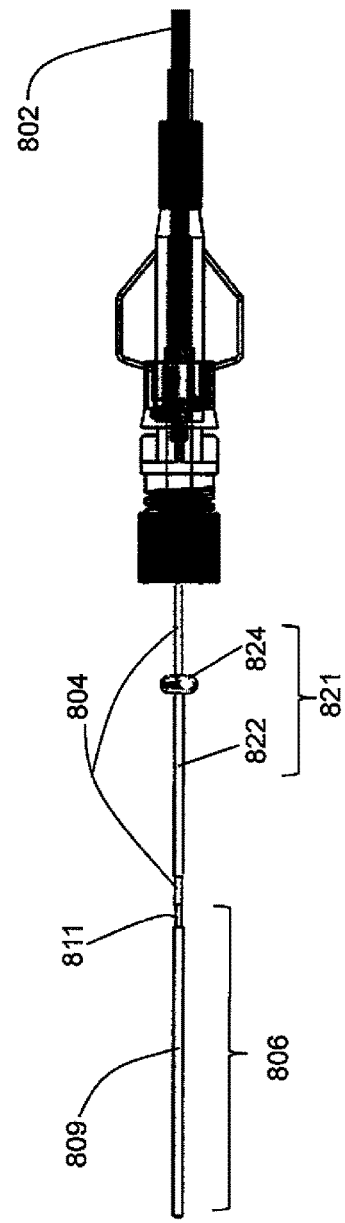
FIG. 15B
FIG. 15C

333
IMPLANT RETRIEVAL DEVICE

CROSS-REFERENCE TO RELATED APPLICATIONS

This application is a U.S. National Phase application under 35 U.S.C. § 371 of International Application No. PCT/US2012/025748, filed Feb. 17, 2012, which designated the United States and which claims priority to U.S. Provisional Patent Application 61/444,652, filed on Feb. 18, 2011, and U.S. Provisional Patent Application 61/537,017, filed on Sep. 20, 2011, each of which is hereby incorporated by reference in its entirety.

This application is also related to U.S. application Ser. No. 12/657,422, filed on Jan. 19, 2010, which claims the benefit of U.S. Provisional Application No. 61/145,964, filed on Jan. 20, 2009, U.S. Provisional Application No. 61/160,230, filed on Mar. 13, 2009, U.S. Provisional Application No. 61/160,670, filed on Mar. 16, 2009, U.S. Provisional Application No. 61/178,910, filed on May 15, 2009, and U.S. Provisional Application No. 61/178,938, filed on May 15, 2009, the disclosures of all of which are incorporated herein by reference in their entirety.

BACKGROUND

The present invention relates to the percutaneous retrieval of implants.

The retrieval of implanted medical devices in the human body can currently be accomplished through a variety of means. Some are retrieved surgically, involving significant trauma to a patient with generally large recovery times. Small medical devices may be retrieved using catheters in percutaneous techniques. However, such capture devices may not consistently and securely engage the implanted device, and repeated attempts to engage the implanted device may pose additional risks, such as perforation of a blood vessel or organ. Therefore, improved devices and methods for retrieving an implant may be desirable.

SUMMARY

Described herein are devices, systems, and methods for the retrieval of a deployed and/or implanted medical device. Examples of a deployed medical device may include an implant, tissue anchor or the like. One variation of a retrieval system may comprise an implant coupled to a a retrieval tether, where the tether extends between the position of the implant within the body to a position outside the body and a retrieval device including a retrieval tether for engaging the retrieval tether outside the body. The retrieval tether may be used as a guide element for advancing the retrieval device to the implant within the body. After the retrieval device is advanced to the implant, the retrieval tether may be used to capture and remove the implant. All procedures may be performed as part of a percutaneous procedure.

In one variation, an implant retrieval device may comprise an outer elongate body, an inner elongate body within the outer elongate body, an actuator slidably coupled to the inner elongate body, and a retrieval cable. The outer elongate body may have a first longitudinal lumen extending therethrough, and the inner elongate body may comprise a second longitudinal lumen and a stop located within the second longitudinal lumen at a distal portion thereof. The actuator may be slidably coupled to the inner elongate body and the retrieval cable may be slidably disposed within the second longitudinal lumen of the inner elongate body and connected to the actuator such that the retrieval cable at least partially surrounds the stop. The proximal ends of the retrieval cable may be attached to the actuator. In some variations, the outer elongate body may comprise a first pre-shaped curve with a first radius of curvature and a second pre-shaped curve located distal to the first pre-shaped curve, where the second pre-shaped curve has a second radius of curvature that is less than the first radius of curvature. The first radius of curvature may be, for example, about 1.25 inches and the second radius of curvature may be, for example, about 0.17 inch or about 0.25 inch. In one variation, the first pre-shaped curve may comprise a material with a first durometer and the second pre-shaped curve may comprise a material with a second durometer that is higher than the first durometer. The distal end of the outer elongate body may have an atraumatic tip. In some examples, the outer elongate body may have at least one radiopaque marker. The position of the retrieval cable with respect to the stop may vary according to the position of the actuator. In some variations, the retrieval cable may be constructed from a shape memory alloy. The inner elongate body may have a first suture capturing configuration and a second suture securing configuration, where in the first configuration, the actuator is located in a distal position and in the second configuration, the actuator is located in a proximal position. In the first configuration, the retrieval cable may form a loop that is distal to the stop and in the second configuration, the loop may contact the distal end of the stop. Optionally, the inner elongate body may further comprise a retainer configured to secure the position of the actuator with respect to the inner elongate body. For example, the retainer may comprise an O-ring, and may optionally comprise a sleeve proximal to the O-ring. In some variations, the distal end of the outer elongate body may be adapted to receive an anchor. Optionally, an implant retrieval device may further comprise a motor configured to adjust the position of the actuator.

Also described herein is an implant retrieval system. The implant retrieval system may comprise an implant comprising a retrieval tether engaged to the implant, an outer elongate body having a first longitudinal lumen extending therethrough, and an inner elongate body within the first longitudinal lumen. The inner elongate body may comprise a second longitudinal lumen, a stop located within the second longitudinal lumen at a distal portion of the second longitudinal lumen, an actuator slidably coupled to the inner elongate body, and a retrieval cable slidably disposed within the second longitudinal lumen and connected to the actuator such that the retrieval cable at least partially surrounds the stop. The retrieval tether may have a length at least as long as the length of the outer elongate body, and may be, for example, about 100 cm or greater in length.

Another variation of an implant retrieval device may comprise an outer elongate body, an inner elongate body slidably retained within the outer elongate body, where the inner elongate body comprises a first longitudinal lumen and a second longitudinal lumen, where the first and second longitudinal lumens are separated by a partition, a retrieval cable slidably disposed within the first and second longitudinal lumens an actuator slidably coupled to the inner elongate body, and a retainer configured to secure the position of the actuator with respect to the inner elongate body. The proximal ends of the retrieval cable may be attached to the actuator. The retrieval cable may cross between the first and second longitudinal lumens at a distal portion of the inner elongate body, where the retrieval cable crossing defines a loop.

Also described herein is a method of percutaneously retrieving a previously deployed anchor, the anchor having a retrieval tether extending from the tissue anchor to outside a patient body. The method of retrieving may use a retrieval catheter having an outer elongate body, an inner elongate body and a snare, and may comprise extending a snare from a retrieval catheter, capturing the retrieval tether with the snare, securing the retrieval tether in an inner elongate body, threading the retrieval tether through the outer elongate body, withdrawing the inner elongate body with respect to the outer elongate body, advancing the outer elongate body to the anchor location, applying proximally directed force on the retrieval tether to capture the anchor within the outer elongate body, and withdrawing the outer elongate body from the patient, where the outer elongate body contains the anchor.

In an embodiment, there is a medical apparatus for retrieving a medical implant with an attached retrieval tether from a human body. The apparatus has an outer elongate body having a proximal end, a distal end, and a lumen extending therethrough the outer elongate body. There is an inner elongate body having a proximal end, a distal end, and an inner body lumen extending therethrough the inner elongate body. The inner elongate body can be configured to slidably transit the lumen of the outer elongate body. The inner elongate body has a partition positioned within and substantially near the distal end of the inner body lumen. There is a snare extending through the inner body lumen. The snare has a proximal end, a distal end and a body therebetween. The distal end of the snare being configured to slidably engage said partition. Furthermore, there can be a push rod attached to substantially the proximal end of the snare. A sleeve may be slidably positioned over the push rod and the inner elongate body. The sleeve can be positioned substantially near the proximal end of the elongate body. A restraint is used for generally locking the position of the sleeve.

Also described herein is a medical grade implant with a flexible retrieval tether engaged to the implant, wherein the flexible retrieval tether is sufficiently long enough to be retrieved through a catheter or other percutaneous retrieval apparatus.

There is also described a method of percutaneously retrieving a previously deployed anchor, where the anchor is attached to a retrieval tether extending from the tissue anchor to outside a patient body. The method may comprise using a retrieval catheter having an outer elongate body, an inner elongate body and a snare. The method of retrieval may comprise extending a snare from a retrieval catheter, capturing one or more retrieval tether(s) with the snare, securing the captured retrieval tether(s) in an inner elongate body, threading the captured retrieval tether(s) through the outer elongate body, withdrawing the inner elongate body from the outer elongate body, capturing at least one implant by applying proximally directed force on the retrieval tether(s) through the outer elongate body; and withdrawing the outer elongate body from a patient, wherein the outer elongate body contains at least one implant.

BRIEF DESCRIPTION OF THE DRAWINGS

FIG. 1 depicts an embodiment of an implant retrieval device.

FIG. 2 depicts an embodiment of the distal section of an implant retrieval device.

FIG. 3 depicts an embodiment of an improved medical device with a retrieval tether.

FIGS. 15A-15C depict perspective views of one variation of an implant retrieval device.

DETAILED DESCRIPTION

Figure 4A:
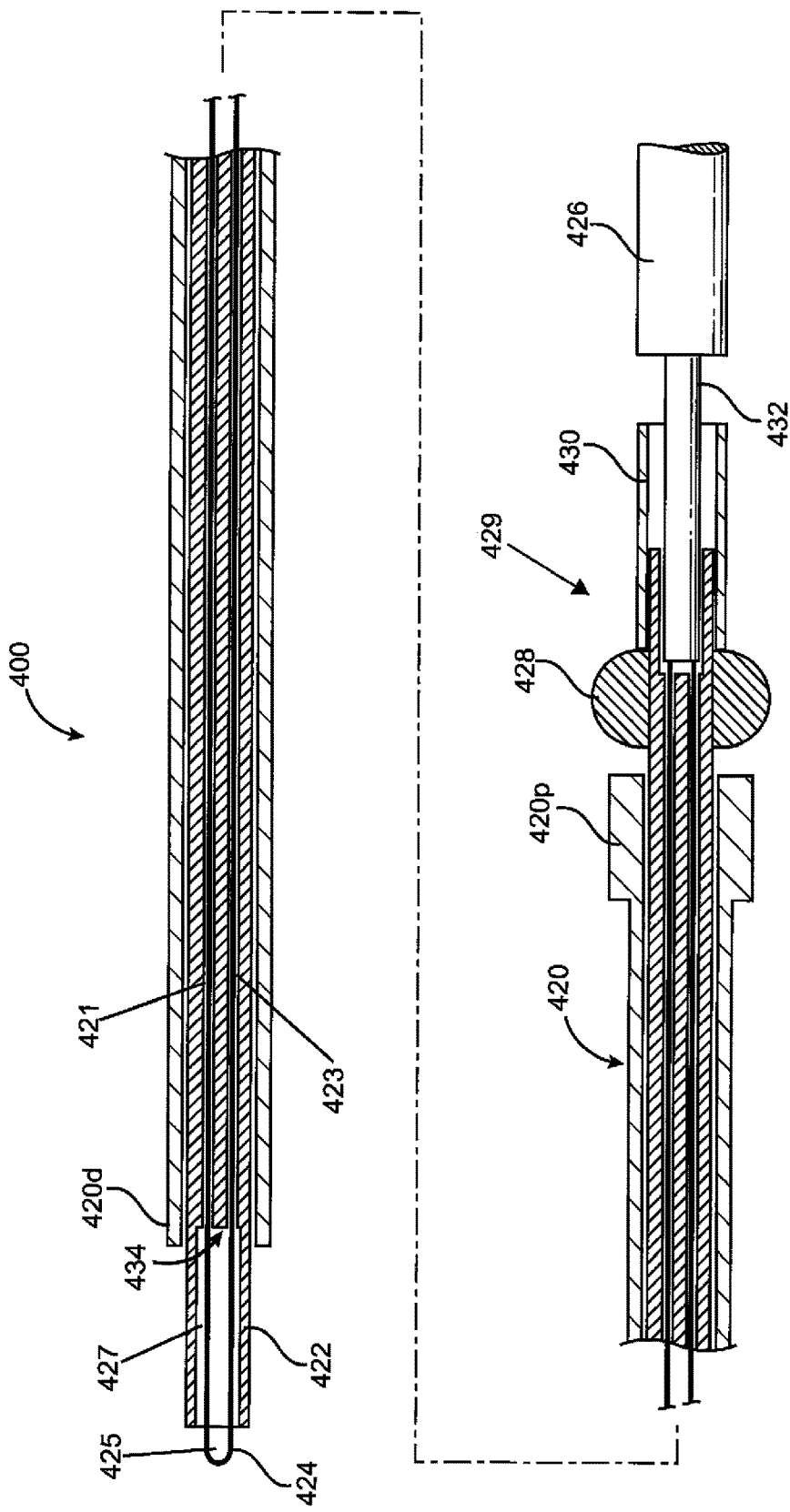
FIG. 4A depicts a cross-section of one variation an implant retrieval device.

Described herein are devices and methods for the percutaneous retrieval of medical devices from within the human body.

In an embodiment, there is a medical device in a patient body, the medical device having a retrieval tether attached to it, with the retrieval tether extending from the medical device to outside the body via a percutaneous entry point. The retrieval tether may be sufficiently robust to sustain an external force (e.g., a proximally directed force) to draw an implant or other medical device from inside a patient into a retrieval device without breaking.

Also described is a medical device for retrieving the implant. In an embodiment, there is a medical device adapted for use in a percutaneous procedure, where the medical device is coupled to a retrieval tether. An implant device may have an outer elongate body with a lumen extending therethrough. An inner elongate body within the outer elongate body may have a snare, retrieval cable or other device for capturing a retrieval tether that may be coupled to the medical device. The inner elongate body may generally suitable for threading the retrieval tether through the outer elongate body.

Once the retrieval tether is threaded through the outer elongate body, the outer elongate body may be advanced to abut the implant. In one aspect, the outer elongate body may be guided to the implant via a guide element (e.g., a guide catheter and/or guide tunnel). In another aspect, the outer elongate body may be guided to the implant by following the retrieval tether and/or an implant tether (i.e., a tether that is part of the implantable medical device). In another aspect, the outer elongate body may be guided to the implant through a combination of following the retrieval tether and/or implant tether and guidance from an additional device (e.g., a guide catheter, guide tunnel, or guide wire). The outer elongate body may have a shaped distal section. The outer elongate body may have an atraumatic tip. The outer elongate body may have a uniform (circular) tip, or a tip having a preformed, irregular shape.

The implant that is retrieved may be made from shape memory metal, or other biocompatible material. A retrieval tether may be attached to a segment or section of the implant, and the implant be configured to assume a configuration that allows it to be retrieved (e.g., with the application of force, it may assume a configuration with a narrower profile, and/or may release the tissue to which it is engaged). An implant retrieval device may be sized and shaped according to the size and shape of the implant that is to be retrieved. In an embodiment, the outer elongate body of an implant retrieval device may have an interior lumen that is sized and shaped to retrieve and retain the implant without deforming or altering the shape of the implant. In another variation, the implant may be deformed (e.g., compressed to a narrower profile) as it is drawn into in the lumen of the outer elongate body. The implant may be compressed, restrained, constrained or plastically deformed as it is retrieved into the lumen of the outer elongate body. Generally, the retrieval tether may be connected to a position or location on the implant that can facilitate the uptake of the implant in to the retrieval catheter, such as a point where the implant may naturally or easily collapse, deform or engage with the outer elongate body.

In an embodiment, the outer elongate body and inner elongate body may operate together and form a retrieval catheter. The retrieval catheter may be configured to retrieve implants deployed previously in the same procedure (e.g., in the same treatment session, any procedure where the patient has not been closed up and sent home, etc.). The implants may have a retrieval tether, extending from a location on the implant within a patient's body to a location outside the patient's body. The retrieval tether may be long enough to sufficiently traverse the distance from implant within the body to a location outside the body, and may optionally have additional length outside the body to facilitate operation with the retrieval catheter, and any other catheter or percutaneous procedures and devices being used on the patient.

In an embodiment, the outer elongate body may be constructed from any of a variety of techniques and materials as are used in medical catheters. In an aspect the outer elongate body may be a braided round wire shaft having a PTFE (polytetrafluoroethylene) liner with a nylon jacket with or without BaSO4 or similar for visualization. In another aspect, the outer elongate body may be a blend of polymer, such as nylon or Pebax®, or alternatively all Pebax® or all nylon. The internal diameter (ID) and outer diameter (OD) may be uniform along substantially the entire length of the outer elongate body. On the proximal section, valve units may be used to allow additional fluids or devices to access the lumen within the outer elongate body. The distal tip section of the elongate outer body may be generally more atraumatic than the overall length of the outer elongate body. The distal tip section may be a PTFE liner with 72D Pebax®, Nylon, or similar polymer blend (for shape retention). Different durometer materials may be used to vary the stiffness of the distal section. For example, the proximal and distal portions of the outer elongate body may comprise materials having different durometers (e.g., the proximal portion may be more flexible than the distal portion). The distal tip of the outer elongate body may be made of yet another material with a different durometer (e.g., to help prevent tissue trauma). For example, the distal tip region of the distal portion of the outer elongate body may be soft and have a durometer between about 25 D to about 40 D, e.g., about 30 D, about 35 D. The proximal portion of the distal portion of the outer elongate body (proximal to the distal tip region) may be a transitional region having a durometer between about 35 D to about 60 D, e.g., 50 D, 55 D, 60 D. A curved portion of the outer elongate body proximal to the transitional region may have a durometer between about 65 D to about 80 D, e.g., about 65 D, 72 D, 78 D. A proximal portion of the outer elongate body may have a durometer between about 20 D to about 60 D, e.g., about 25 D, 35 D, 45 D, 50 D. In various aspects the durometer of the material may be selected for the anatomy of the body where the device may be used, the presence of a support structure (such as a catheter), and the type of implant being recovered. In an aspect, a softer durometer may be selected if the outer elongate body is used to track over a tether without being held inside a catheter. One or more visualization markers, such as platinum iridium, may be used. The most distal section may be a lower durometer Pebax®. The lumen on the distal portion of the outer elongate body begins with a portion sized to allow the capture or retention of an implant. The distal lumen opening may be sized to hold part or all of an implant. The outer elongate body lumen should also be sized to allow the passage of an inner elongate body therethrough.

Examples of materials which may be suitable for any or all of the regions or components of a devices described herein include polymers, such as polyether-block co-polyamide polymers (e.g., PEBAX® polyether block amide copolymer), copolyester elastomers, thermoset polymers, polyolefins (e.g., polypropylene or polyethylene, including high-density polyethylene (HDPE) and low-density polyethylene (LDPE)), polytetrafluoroethylene (e.g., TEFLON™ polymer) or other fluorinated polymers, ethylene vinyl acetate copolymers, polyamides, polyimides, polyurethanes (e.g., POLYBLEND™ polymer), polyvinyl chloride (PVC), fluoropolymers (e.g., fluorinated ethylene propylene (FEP), perfluoroalkoxy (PFA) polymer, polyvinylidenefluoride (PVDF), etc.), polyetheretherketones (PEEKs), silicones, and copolymers and blends thereof. Examples of polyamides include Nylon 6 (e.g., ZYTEL® HTN high performance polyamides from DuPont™), Nylon 11 (e.g., RILSAN® B polyamides from Arkema Inc.), and Nylon 12 (e.g., GRILAMID® polyamides from EMS-Grivory, RILSAN® A polyamides from Arkema Inc., and VESTAMID® polyamides from Degussa Corp.). In addition the polymer material may include metal braids of stainless steel, nickel-titanium or other alloys.

In another embodiment, the outer elongate body may have a preformed shape, for example, along the distal portion or the tip of the elongate body. A preformed shape may assist the navigation of the outer elongate body through the patient vasculature. Alternatively specific shaping of the tip may assist in the mating of the tip aperture to that part of the implant having a retrieval tether and/or implant tether coupled to it. In some embodiments, the outer elongate body may be advanced through a guide element such as a guide tunnel and/or guide catheter. In this embodiment, the retrieval tether and/or implant tether may also extend through the guide tunnel or guide catheter, and/or extend through a lumen of the outer elongate body. In one variation, the guide catheter and/or guide tunnel may have a particular shape, with one or more openings or apertures through which the retrieval catheter may exit to contact the deployed and/or implanted device. In some variations, the location and size of the apertures, and/or the curvature of the guide element may be configured to cause the retrieval catheter to exit the guide element at a particular orientation and/or angle. In an embodiment, the inner elongate body may be made of a polymer having a low coefficient of friction, such as high density polyethylene (HDPE). The low coefficient of friction may allow the inner elongate body to generally slide through the lumen of the outer elongate body with ease.

The inner elongate body may also have a lumen extending through it. The lumen may contain a snare (e.g., comprising a retrieval cable), and a partition or stop or snare trap. The snare may extend along the entire length of the inner elongate body, and may be activated from the proximal region of the inner elongate body. In an aspect of the inner elongate body, there may be a snare that extends along the length of the inner elongate body, and extends through the lumen of the inner elongate body. The snare may be wire, suture, cable, or other suitable material. At the distal end of the snare, there may be a loop, hook, barb or other feature to assist in the capture of a tether (e.g., a retrieval tether and/or implant tether). At the proximal end of the snare, there may be a rod (used for pushing or pulling the snare) attached to the snare. The inner lumen of the inner elongate body may also have a partition, stop, post, trap or other feature for allowing the engagement of the snare to the snare trap. In an embodiment, there may be more than one lumen in the inner elongate body, such that either a single cable may be used as a snare that extends from the exterior proximal end of the inner elongate body, to the distal tip, the looped back through another lumen of the inner elongate body, and back out the proximal end of the inner elongate body. In this embodiment, the snare cable may be about twice the length of the inner elongate body.

In an embodiment, the inner elongate body is coaxial with the outer elongate body, where the inner elongate body positioned within the lumen of the outer member. The inner elongate body may have a snare that can be moveable independent of the inner elongate body to some degree, or completely separate in movement ability. The snare may be extended forward of both the inner and outer members, and a tether (e.g., a retrieval tether and/or implant tether) fed through the snare. The tether may be engaged by a capture feature of the snare, such as a barb, burr or similar component. Alternatively the tether may be threaded through a loop of the snare. The snare may then be retracted into or toward the proximal end of the inner elongate body, so that the snare and the tether contact the snare trap (e.g., a partition or stop). Once the snare trap is engaged, the tether may be restrained against the snare trap with sufficient force so the tether does not work loose or slip from the snare trap. The restraining force may be provided by a variety of devices. In an aspect, the restraining force may be provided by use of a retainer device, such as a polymer sleeve wrapped around the proximal section of the inner elongate body. The polymer sleeve may slidably engage the rod at the proximal end of the snare, and may be held in place with a clamp, such as an O-ring, slip or other compression device. When the snare is proximally withdrawn, the snare trap may engage with the snare and tether, and the polymer sleeve can be used to hold the relative position of the snare and the inner elongate body. The clamp or compression device may be used to maintain a constant relative position between the snare and inner elongate body.

In an embodiment, the outer elongate body may be advanced over the inner elongate body after the retrieval tether and/or implant tether have been captured and secured. The inner elongate body may be held at a constant relative position to the patient, while the outer elongate body is advanced first over the inner elongate body, and then over the tether. While the inner elongate body is held stationary, the outer elongate body may be advanced distally over the tether and advanced to the position where the implant is located. The inner elongate body may remain outside the patient body the entire time, so the snare may not physically enter the patient body.

In various embodiments, the outer elongate body may be advanced over the tether to the implant. The tether may be a very flexible material, such as a polymer. In other embodiments the tether may be a wire. The tether may be polymer or natural fibers. In an embodiment, a braided polytetrafluoroethylene (PTFE) impregnated polyester fiber may be used. In an aspect the impregnated polyester fiber may be size 4-0. In some embodiments, the tether may be threaded through another elongate body that extends from outside the patient body to a position near where the implant is located. Such elongate bodies may be a guide catheter, guide tunnel, or protective sheath catheter or the like. In still other embodiments, the outer elongate body may track over the tether and through another elongate body. The outer elongate body may be advanced over the tether until the distal tip of the outer elongate body may be in the vicinity of the implant. In some embodiments of the methods described herein, the distal tip of the outer elongate body may physically contact the implant, however the operative method may still be performed if the outer elongate body does not initially contact the implant.

Once the outer elongate body is advanced to a position in close proximity to and/or contacting the implant, the inner elongate body and snare may be proximally withdrawn until the inner elongate body and snare are completely withdrawn from the outer elongate body. The tension on the snare may then be relaxed and the retrieval tether may be removed from the snare trap, and separated from the snare.

Once the distal tip of the outer elongate body is positioned in proximity to the implant, the retrieval tether may be proximally withdrawn by exerting a pulling force on the proximal end of the retrieval tether that is outside the patient body. The retrieval tether may be drawn or pulled manually, or with the assistance of some mechanical advantage (such as a lever arm, winch or other manually controlled device) or with the assistance of a motor. The force on the retrieval tether may cause the implant to be withdrawn into the distal tip of the outer elongate body. Once a sufficient portion of the implant is captured in the distal tip of the outer elongate body (and not enough of the implant remains in tissue to cause serious harm of the implant being suddenly removed), the entire outer elongate body may be withdrawn from the body, with the implant positioned partially or wholly retained inside a distal portion of the elongate body.

Once the implant and outer elongate body are withdrawn from the patient, any additional intended percutaneous or surgical procedures may continue or resume.

Turning now to the figures, it should be understood that items shown in the figures are not to scale with respect to other items or even necessarily to itself. Items may be emphasized in the drawings for clarity, while other elements are de-emphasized or omitted entirely. Elements from one figure to another may not be consistent as either the element is not necessary in every drawing to depict the elements being taught. None of the drawings are to scale, and no scale of specific measurement units should be implied or imputed to these drawings.

In an embodiment, there is an medical implant 300, having a medical device implant 302 with a retrieval tether 304 used as a retrieval tether attached to it (FIG. 3). The retrieval tether may be sufficiently lengthy to extend from an implant position to outside the body. In the case of a percutaneous procedure, the retrieval tether may have a length of 100 centimeters (cm) or more, e.g., 150 cm, 160 cm, 170 cm, 200 cm. In some variations, the retrieval tether may be less than 100 cm, e.g., 50 cm, 60 cm, 70 cm, 80 cm, 90 cm. In an aspect, the implant may be positioned in the heart using a percutaneous technique. If a physician desires to remove the implant for any reason, the implant can be withdrawn using the retrieval tether and a retrieval device, as will be described in greater detail below. In an embodiment, the retrieval tether may be removably attached to the implant, so the retrieval tether may be removed from the implant after it is determined that the implant is properly deployed, and that it need not be removed. In some variations, a retrieval tether that is removable from the implant may be a tether which is threaded through the implant (e.g., through an eyelet or loop of the implant), with both ends of the tether located proximally (e.g., external to the patient's body). Alternatively the retrieval tether may engage the implant via a removable adapter which may be disengaged when desired.

Figure 13:
FIG. 13 illustrates an embodiment of a short snare.

In an embodiment, a retrieval catheter 100 has an outer elongate body 104, an inner elongate body 102 and a retrieval cable or snare 108 that extends coaxially within the inner elongate body (FIG. 1). In some embodiments, the snare may be a long snare (such as is depicted in FIG. 1) and/or may be (or include) a short snare 1300 (such as is depicted in FIG. 13). The inner elongate body may extend coaxially to the outer elongate body, though variations may include embodiments where the outer elongate body may have one or more additional lumens for housing one or more inner elongate bodies. The inner elongate body may be slidable within a lumen of the outer elongate body so the entire length of the inner elongate body may be withdrawn from the length of the outer elongate body. The snare may be made of wire (such as Nitinol or stainless steel or any equivalent material) or a polymer material. The snare generally can be slidable inside the inner elongate body. In an aspect, the snare can be used to capture a retrieval tether 304 of an implantable device by threading the retrieval tether through the snare loop. The snare may then be drawn proximally so it engages a trap or stop, and holds the retrieval tether in place. The capture or threading of the retrieval tether through the snare loop may be done outside of the body. In an embodiment, the distal section of the outer elongate body may have a pre-formed shape 104d or be curved to better fit a desired anatomy (FIG. 2.). The distal end of the inner elongate body 102d may not have a corresponding curve (or have any pre-shaped curve, for example, if the outer elongate body has sufficient stiffness to cause the inner elongate body to follow the same shape as the outer elongate body.

The inner elongate body may have a proximal end 102p and a distal end 102d. A snare 108 may extend through the inner elongate body, and be slidable within the inner elongate body. The snare 108 may have a loop or other feature suitable for capturing a tether (e.g., a retrieval tether and/or implant tether). In an aspect, the snare loop may have a secondary snare threaded through it. Alternatively or additionally, the snare may have one or more barbs for capturing a tether. In another aspect, the snare may have a sticky or tacky segment for adhering to a tether.

Figure 15A:
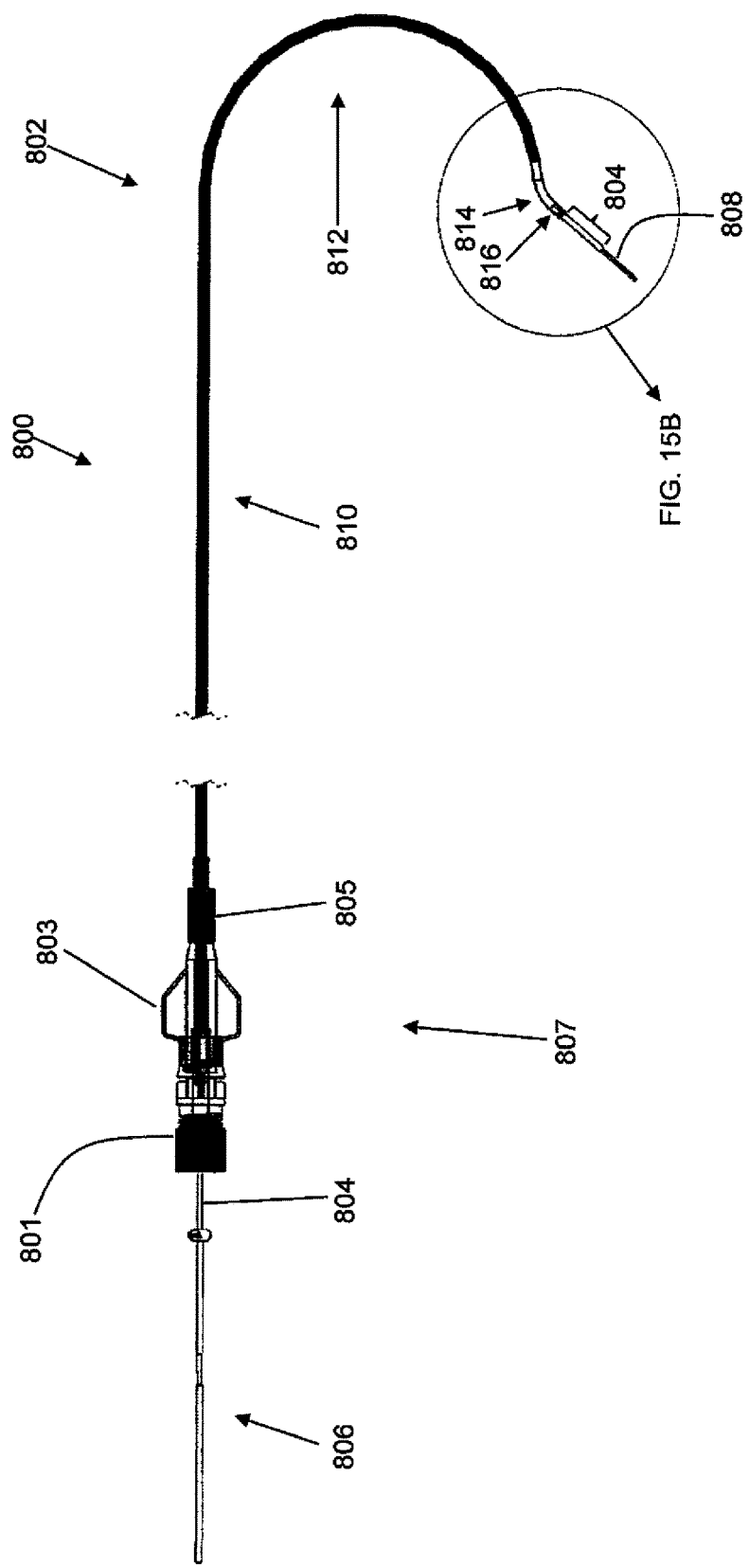

One variation of an implant retrieval device 800 is depicted in FIGS. 15A-15C. Implant retrieval device 800 may comprise an outer elongate body 802 with a longitudinal lumen therethrough, an inner elongate body 804 slidably retained within the outer elongate body 802, an actuator 806 coupled to a proximal portion of the inner elongate body 804, and a retrieval cable 808 slidably disposed within a longitudinal lumen of the inner elongate body 804. As illustrated in FIG. 15A, the inner elongate body 804 may be longer than the outer elongate body 802 such that the inner elongate body 804 extends out of the distal end of the outer elongate body 802. Optionally, the implant retrieval device 800 may also comprise a Touhy borst 801, a Luer connector (e.g., a Luer lock) 803, and a strain relief structure 805 at a proximal portion 807 of the retrieval device 800 which may help to prevent kinking of the outer elongate body. In some variations, a retrieval device may additionally comprise a valve, which may be used for infusion of fluids (e.g., pharmacological agents, contrast agents, saline, etc.) and/or for releasing any fluid pressure that may accumulate in the device during use. The inner elongate body 804 may be made of any materials suitable for catheter devices, such as HDPE or any of the materials previously described. The retrieval cable may be made of any shape memory, polymeric, or metal material, as previously described for snares.

The outer elongate body 802 may comprise one or more pre-shaped curves along its length. For example, the outer elongate body 802 may comprise a first straight portion 810, a first curved portion 812 with a pre-shaped curve, a second curved portion 814 with a pre-shaped curve, and a second straight portion 816. The pre-shaped curves may be determined at least in part according to the curvature of the anatomy through which the retrieval device is to be advanced and/or the shape of any other catheter devices that to be advanced over or through the retrieval device. For example, the radius of curvature of the first curved portion 812 may be selected to correspond with the curvature of a guide catheter through which the outer elongate body is advanced. In some variations, the radius of curvature of the first curved portion may be from about 1 inch to about 2 inches, e.g., about 1.25 inches. FIG. 15B depicts an enlarged view of the distal end of the outer elongate body 802 with the inner elongate body 804 and retrieval cable 808 extending from its distal end. The second curved portion 814 may have a radius of curvature from about 0.15 inch to about 0.4 inch, e.g., about 0.17 inch or 0.25 inch. The second curved portion 814 may be angled with respect to the first curved portion 812, with an angle 815 from about 15° to about 40°, e.g., about 25°, or at least 25°. The second straight portion 816 may have a length from about 2.5 mm to about 4.5 mm, e.g., about 3.5 mm or no more than 3.5 mm. The second straight portion 816 may comprise radiopaque marker 818 and an atraumatic distal-most tip 820. The length of the atraumatic distal tip 820 may be from about 0.2 mm to about 1 mm, e.g., about 0.25 mm, 0.5 mm, etc. As described previously, the mechanical properties (e.g., stiffness, flexibility) and/or the material composition of the outer elongate body may vary along its length and between its different curved and straight portions. In some variations, a proximal portion of the outer elongate body may be more flexible than the distal portion, and the distal tip may be more flexible than the remainder of the distal portion. For example, the first straight portion 810 and the first curved portion 812 may comprise nylon 12, the second curved portion 814 may comprise Pebax® 72D, the second straight portion 816 may comprise Pebax® 55D just distal to the radiopaque marker 818 and the atraumatic tip 820 may comprise Pebax® 35D. The relatively flexible first straight portion 810 and first curved portion 812 may allow the outer elongate body to navigate through tortuous anatomical paths (e.g., through curved vascular paths), while the relatively stiffer second curved portion 814 may help the outer elongate body to contact the tissue to which the device is implanted. For example, the second curved portion may comprise a relatively stiff material (such as Pebax® 72D), have a radius of curvature of about 0.17 inch and an angle of about 25°, which may help the outer elongate body to exit a side opening or aperture of a guide catheter to contact a device that has been deployed near and/or at least partially implanted into a tissue wall. In some variations, at least a portion of the length of the outer elongate body may alternatively or additionally comprise a braided round wire shaft having a PTFE (polytetrafluoroethylene) liner with a nylon jacket with or without BaSO4 or similar material. For example, the first straight portion 810, first curved portion 812, second curved portion 814 and most of the second straight portion 816 (e.g., up to the atraumatic tip 820) may comprise a braided material. In other examples, only the first straight portion 810 and first curved portion 812 may comprise a braided material. Including a braided material with at least a portion of the outer elongate body may help to prevent kinking and may increase flexibility of the outer elongate body.

FIG. 15C depicts an enlarged view of the proximal portion 807 of the implant retrieval device 800, with the inner elongate body 804 extending from the proximal end of the outer elongate body 802 and the actuator 806 coupled to the inner elongate body. The actuator 806 may be connected within the inner elongate body 804 to the retrieval cable 808, where advancing the actuator 806 in a proximal direction reduces the size of the loop defined by the retrieval cable 808 and advancing the actuator in a distal direction increases the size of the retrieval cable loop. The actuator 806 may comprise a handle 809 and a rod 811, where the handle may have a larger diameter than the rod. The retrieval device 800 may also comprise a retainer that may be used to secure the location of the slidable actuator 806. For example, the retainer may maintain the actuator 806 in a proximal position in order to secure cables and/or tethers that are captured by the retrieval cable loop. One variation of a retainer 821 may comprise a sheath 822 slidably disposed over the inner elongate body 804 and a clamp 824. The diameter of the sheath 822 may be the same as, or smaller than, the diameter of the handle 809, but larger than the diameter of the rod 811. The clamp 824 may be an O-ring or any other suitable fastener. In the configuration depicted in FIG. 15C, where sheath 822 and the claim 824 are both disposed over the inner elongate body 804, the actuator 806 may move with respect to the inner elongate body. To lock the actuator 806 in a proximal position (e.g., in a position that retracts the retrieval cable 808 sufficiently to capture and/or secure one or more cables or tethers), the retainer 821 may be slid proximally such that the sheath 822 and the clamp 824 are disposed over the rod 811, and the clamp 824 clamps over the rod 811. The length of the sheath 822 may be adjusted to vary the lock position of the actuator 806. In some variations, the proximal-most portion of the inner elongate body may comprise a lip to help prevent the clamp from unintentionally disengaging from the rod (e.g., by sliding off the rod and back onto the inner elongate body). The various configurations, embodiments, and uses of a retrieval device (such as retrieval device 800) will be described in greater detail below.

FIGS. 4-7 depict cross-sectional views of a retrieval device (e.g., a retrieval catheter) that may be used for retrieving an anchor that has already been deployed and/or fully released from an anchor delivery catheter. The retrieval catheter may be adapted to receive an implant tether (which may be used to couple multiple implants together), and/or one or more retrieval tethers attached to an implant to be removed. The retrieval devices described herein may be used to retrieve a variety of implants, such as the implants described in U.S. Pat. No. 6,702,826; U.S. Pat. No. 7,166,127; U.S. Pat. No. 6,718,985; U.S. patent application 2002/0095175; and U.S. Pat. No. 6,986,775. One or more retrieval tethers may be included with any of these implants to help facilitate their retrieval.

The implant retrieval device 400 shown in FIG. 4A may have an outer elongate body 420 with a distal end 420d and a proximal end 420p. The outer elongate body 420 may have curved and straight portions and other features as described above, but such features are omitted in the subsequent drawings for the sake of clarity. The outer elongate body 420 may be used as a retrieval catheter and may be configured to retrieve a device that has been implanted into tissue and/or deployed at or near tissue. The outer elongate body 420 may slide coaxially within a guide element (e.g., a guide catheter and/or a guide tunnel). The diameter of the outer elongate body may vary depending on the inner diameter of the guide element through which it is advanced. The outer elongate body 420 may have curved and straight portions and other features as described above, but such features are omitted in FIG. 4A for the sake of clarity. Contained coaxially within the outer elongate body 420 is an inner elongate body 422, which may have a cable or a wire snare or other filament-like material extending through it. The inner elongate body 422 may be a dual-lumen sheath and may comprise two longitudinal lumens extending along at least a portion of its length. For example, the inner elongate body 422 may comprise a first lumen 421 and a second lumen 423 separated by a partition 434. In some variations, the first and second lumens 421, 423 may be formed from a single lumen (e.g., a distal lumen 427) that is separated by a stop or partition (e.g., the partition 434). While the lumens 421, 423 only extend along a portion of the total length of the inner elongate body, in other variations, an inner elongate body may have one or more lumens that extend along the entire length of the inner elongate body. Lumens may be entirely enclosed in the inner elongate body or may be at least partially open. More generally, lumens may be channels, slits, slots, conduits, canals, ducts, or cavities that may be at least partially or fully enclosed within the inner elongate body. Lumens may also be connected to each other, for example, at the distal end of an elongate body or at a location along an intermediate length of the elongate body. In an embodiment, a retrieval cable 424 may extend from the proximal end of the inner elongate body 422 (e.g., through the first lumen 421) to the distal end of the inner elongate body and back to the proximal end (e.g., cross the partition 434 into and through the second lumen 423), forming a loop 425 at the distal end. The retrieval cable 424 may at least partially surround the a stop or partition, and in some embodiments, may entirely surround or encircle a stop or partition. In some variations, a retrieval cable may be a single filament extending from the proximal end to distal end of the inner elongate body without looping back to the proximal end (not shown). The distal end of a single filament retrieval cable may have a capture lasso, where the capture lasso may be a variety of releasable attachments (e.g., hooks, loops, etc.). The proximal end(s) of the retrieval cable 424 may be attached to a proximal actuator comprising a push rod 432, which may optionally be attached to a handle 426. The loop 425 may be used to capture the various tethers (e.g., implant tethers, retrieval tether, and/or cables) extending from the implanted and/or deployed device. In some variations, the implant and/or retrieval tethers extending from the implanted and/or deployed device may extend out of the proximal end of a guide element (e.g., a guide catheter or guide tunnel) as will be described below.

Figure 4B:
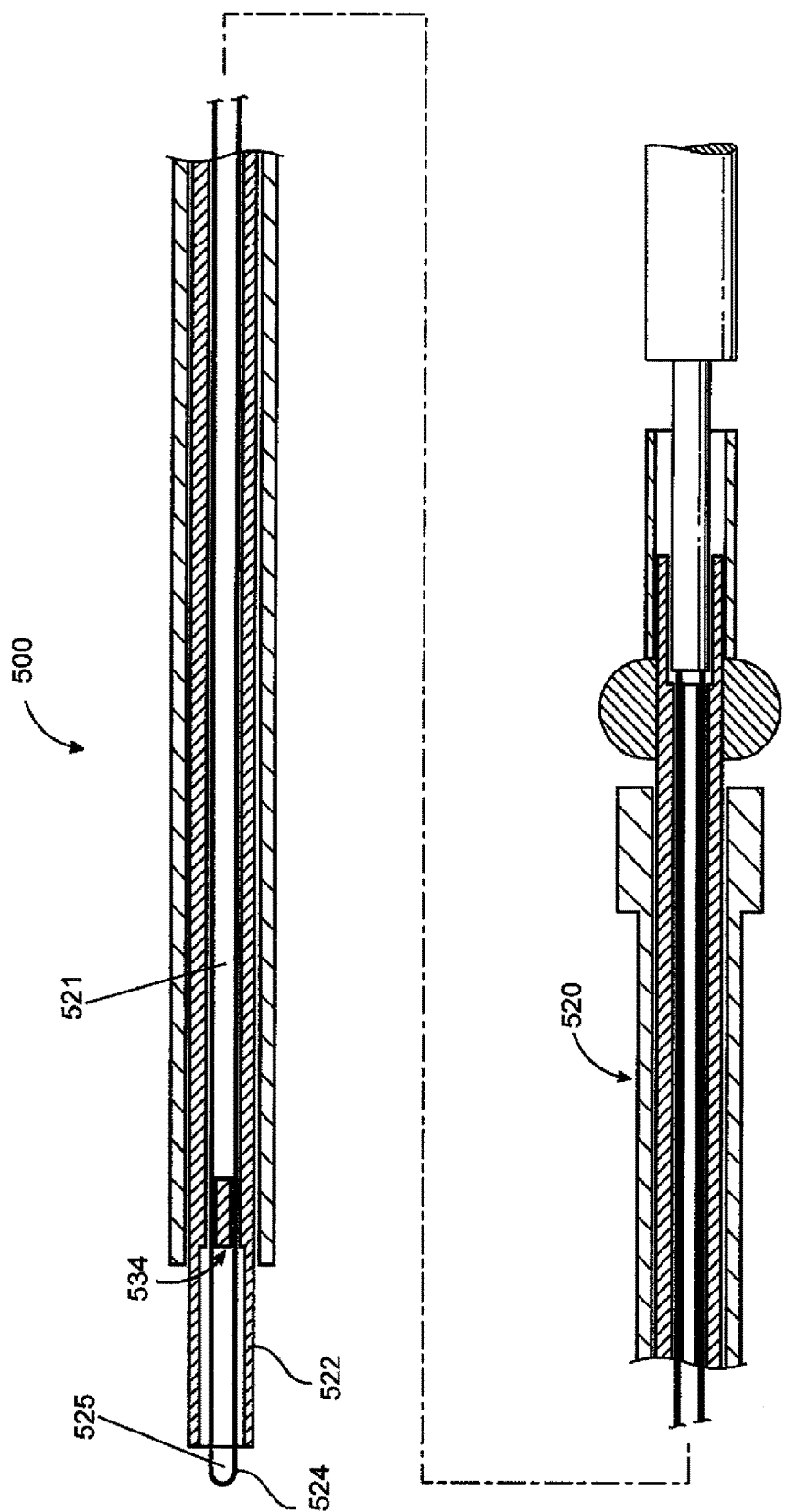
FIG. 4B depicts a cross-section of another variation of an implant retrieval device.

In some variations, the inner elongate body of an implant retrieval device may comprise a single lumen and a stop located at a distal portion of the lumen. FIG. 4B depicts one variation of an implant retrieval device 500 comprising an outer elongate body 520, an inner elongate body 522 with a single longitudinal lumen 521 extending therethrough and a stop 534 located within the longitudinal lumen 521 at a distal portion, and a retrieval cable 524 slidably disposed within the longitudinal lumen 521. The retrieval cable 524 may be connected to an actuator and may be looped such that it at least partially surrounds (and in some variations, may entirely surround or encircle) the stop 534. The portion of the retrieval cable 524 that is distal to the stop 534 may form a loop 525 that may be used to capture one or more tethers and/or cables. The outer elongate body 520 may have curved and straight portions and other features as described above, but such features are omitted in FIG. 4B for the sake of clarity. The retrieval device 500 may be used in a similar or identical manner to the retrieval device 400, and may be used in similar or identical procedures and methods, which will be described further below.

The position of the retrieval cable relative to the inner elongate body and the size of the loop that it forms at the distal end may be adjusted by moving the push rod relative to the inner elongate body. Referring back to FIG. 4A, advancing or retracting the push rod 432 or handle 426 may enlarge or reduce the size of the loop 425 at the distal tip. When the desired size or tension of the loop 425 is achieved, a retainer 429 may be positioned in a way to hold the relative position of the push rod 432 and the inner elongate body 422 such that the tension or size of the loop or lasso does not change. For example, a retainer 429 may comprise a slidable sheath 430 and a clamp 428, and may be positioned at or near the proximal end of the inner elongate body to help keep the inner elongate body 422 and the push rod 432 in actual engagement. While the clamp 428 may initially be located over the inner elongate body 422, it may be moved to clamp the push rod 432. This may prevent the push rod 432 and handle 426 from being advanced distally, since the handle 426 would press against the slidable sheath 430, which would in turn press against the clamp 428, which would be stopped against the junction of the push rod 432 and the inner elongate body 422. In some variations, the proximal-most portion (e.g., the proximal edge) of the inner elongate body may comprise a lip that may help the clamp to better engage the push rod. The clamp may be an O-ring, clamp or other fastener capable of holding the push rod and dual lumen sheath in about a constant axial orientation, and in some variations, the clamp may simply be a slidable tubular spacer element.

Figure 5:
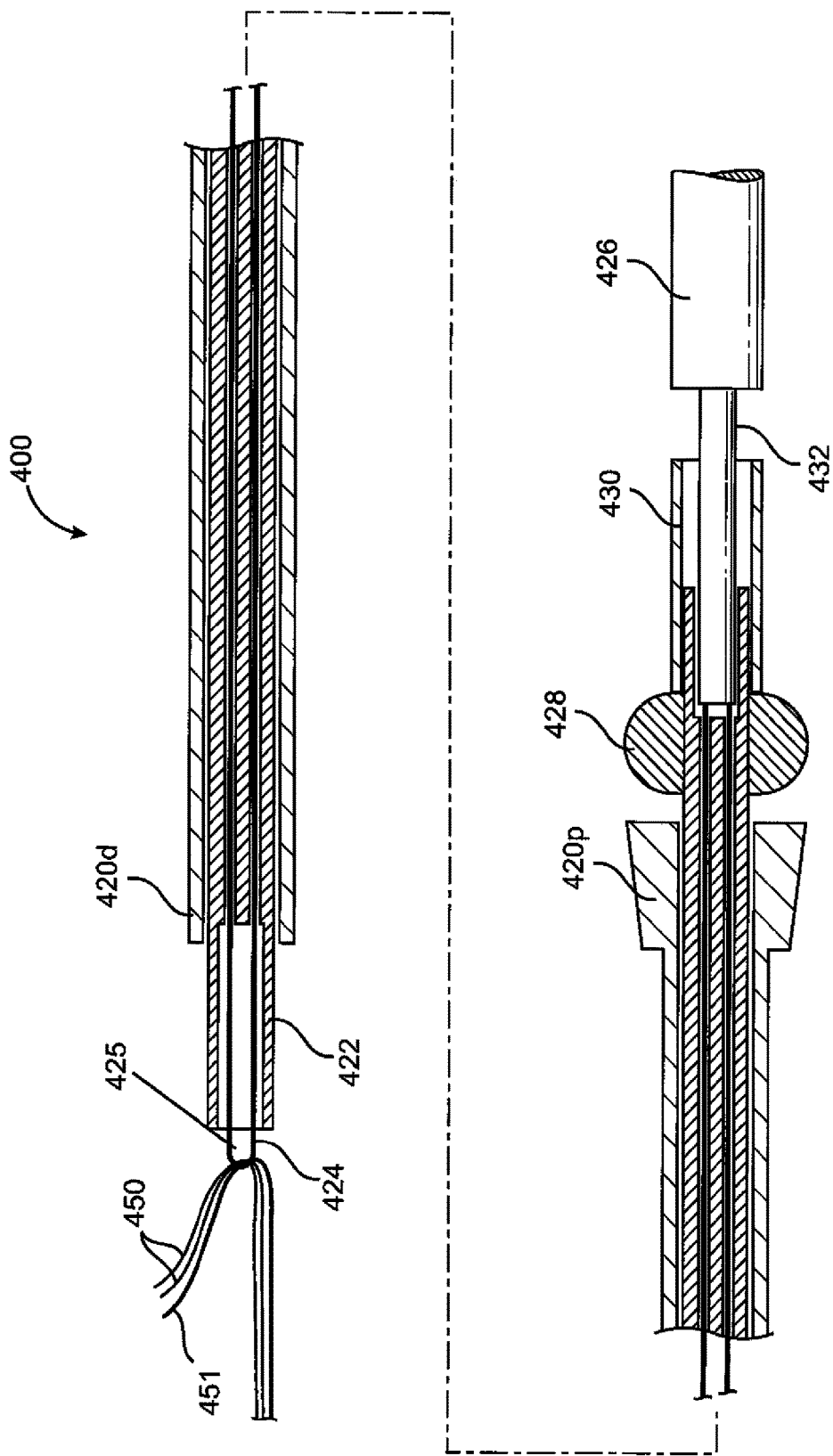
FIGS. 5-7 depict cross-sectional views of an implant retrieval device in various configurations during use.

FIG. 5 depicts the implant retrieval device 400 as it captures one or more cables and/or tethers. For example, the device to be retrieved may comprise one or more retrieval tethers 450 and/or one or more implant tethers 451. An implant tether may be a part of the device that is to remain within a patient body as part of treatment, while a retrieval tether may be withdrawn from the patient at the end of a procedure if it is determined that the device need not be retrieved at that time. For example, an implant tether may be used to couple a plurality of tissue anchors together, where tensioning the implant tether may cinch tissue, as may be desired during a procedure for the treatment of mitral valve regurgitation. The retrieval tether 450 and/or the implant tether may be snared or captured by the loop 425 that is formed by retrieval cable 424. The retrieval tether 451 (and optionally the implant tether 451) may be threaded through the snare loop 425. The retrieval cable 424 may be advanced and retracted through the inner elongate body (which may have one or more lumens, as described above). In various embodiments, the capture or snaring of the retrieval tether and/or implant tether maybe done outside the patient body, with the device operator manually threading the tethers through the loop 425, or using a second snare (not shown) to thread the tethers through the loop 425 of the retrieval device. The size of the loop 425 may be adjusted by distally advancing (to enlarge the loop for threading the tethers) or proximally withdrawing (to shrink the loop for capturing the tethers) the handle 426 and/or push rod 432.

Figure 6:
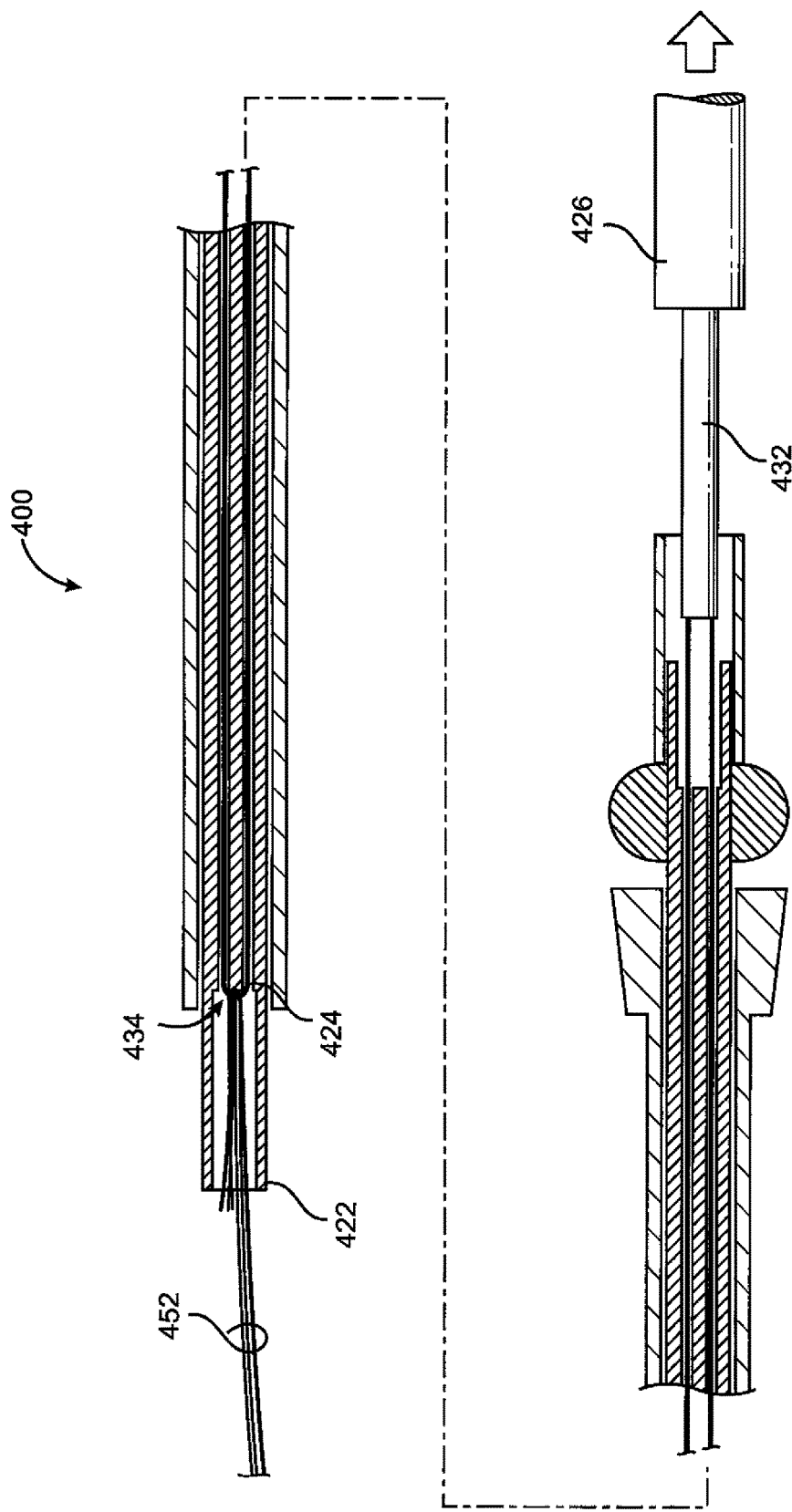

FIG. 6 depicts the retrieval device 400 in a configuration where the retrieval tether and/or the implant tether (collectively annotated as a bundle 452) have been captured and drawn into the inner elongate body 422 by the looped retrieval cable 424. An operator may pull the handle 426 proximally in the direction of the open arrow such that the captured bundle 452 is pressed against the partition 434 (or a stop, such as stop 434) by the retrieval cable. This may help to ensure the one or more tether(s) are held firmly in place. In some variations, there may also be a section of a single lumen tubing at the distal end of the inner elongate body, so the tether(s) may be secured in the inner elongate body through the tension created by the retrieval cable against the partition, as well as the compression created by pulling the tether(s) into the single lumen distal section.

Figure 7:
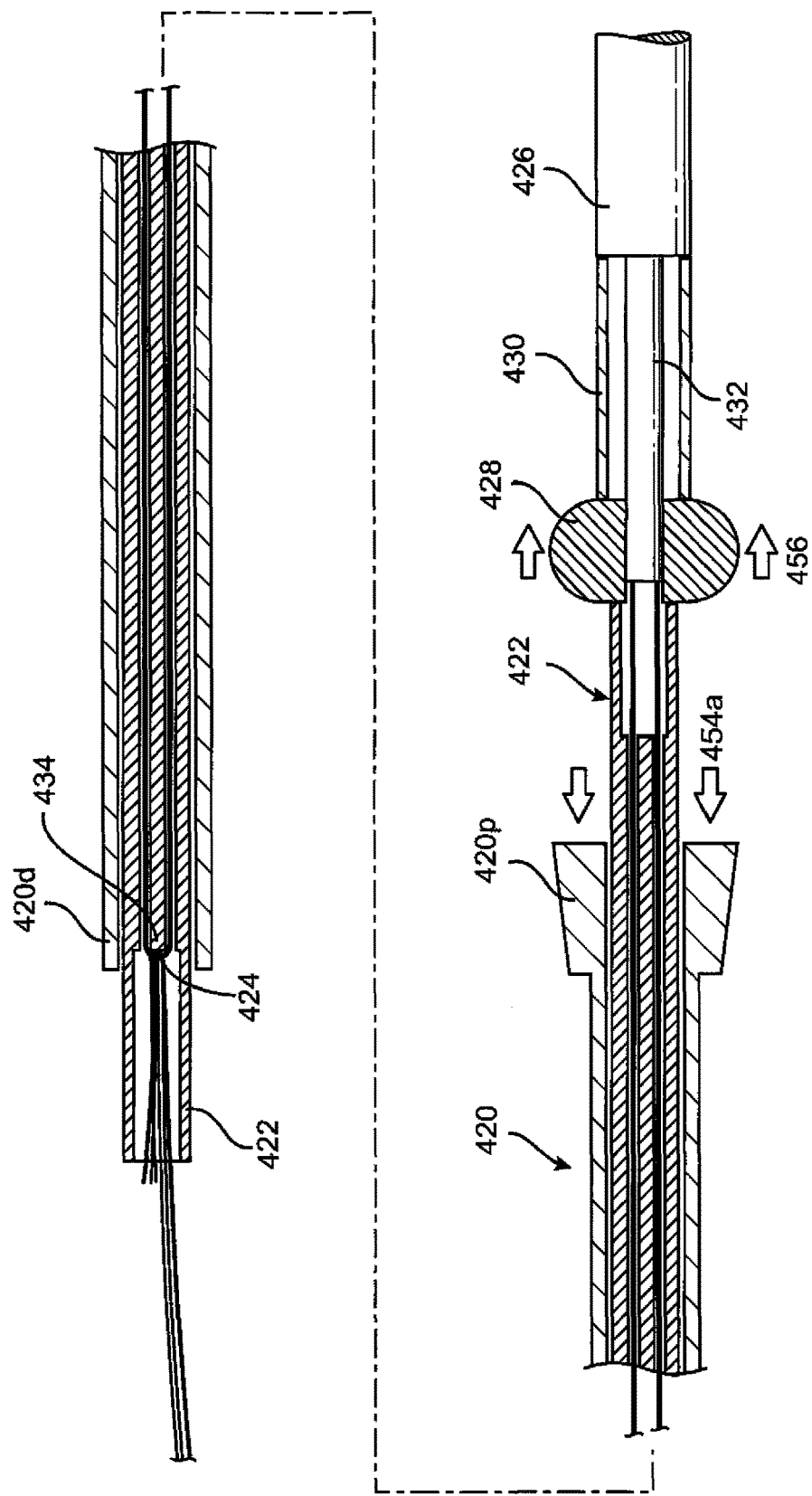

FIG. 7 depicts the retrieval device 400 in a configuration where the retrieval tether and/or the implant tether have been secured and locked against a partition or stop. Once the retrieval cable 424 captures and presses the tether(s) against the partition 434 or stop near or within the distal section 420d of the outer elongate body 420, the slidable sheath 430 may be withdrawn proximally to abut the handle 426. The clamp 428 may then be moved proximally clamp over the push rod 432, which may act to restrain the sheath 430 and the push rod 432 in position relative to each other. The inner elongate body may now be held stationary on the proximal side (e.g., by the operator, external to the patient body) while the outer elongate body 420 can be advanced over the retrieval tether and/or implant tether into the patient body to abut, or be in close proximity to, the deployed and/or implanted device (which is attached to the distal end of the retrieval tether). In an embodiment, the outer elongate body may be advanced through a guide element (such as a guide catheter and/or guide tunnel). In another embodiment, the outer elongate body may be advanced through the patient vasculature without being advanced within a guide element, and may use the retrieval tether(s) and/or implant tether to reach the deployed and/or implanted device. Alternatively or additionally, the outer elongate body may also be advanced over a guide wire, for example, using a separate internal guidewire lumen, or rapid exchange type of guidewire lumen. In various embodiments, the outer elongate body can be advanced manually from outside the patient body, tracking over the inner elongate body. The inner elongate body may be axially stationary, and may be located completely outside the body while the outer elongate body advances to the target site within the patient. The inner elongate body 422 may be held using a proximally-directed manual force, or in combination with the position retaining device able to exert a holding force 456 on the sheath 430. In various embodiments the arrangement is designed to ensure tension is retained on the retrieval cable 424, retrieval and/or implant tether(s), against a hard stop or partition 434 to help ensure the retrieval and/or implant tether(s) do not slip out or come loose during the advancement of the outer elongate body 420 towards the implanted and/or deployed device. An advancing force 454a may be applied to advance the outer elongate body distally.

Figure 8:
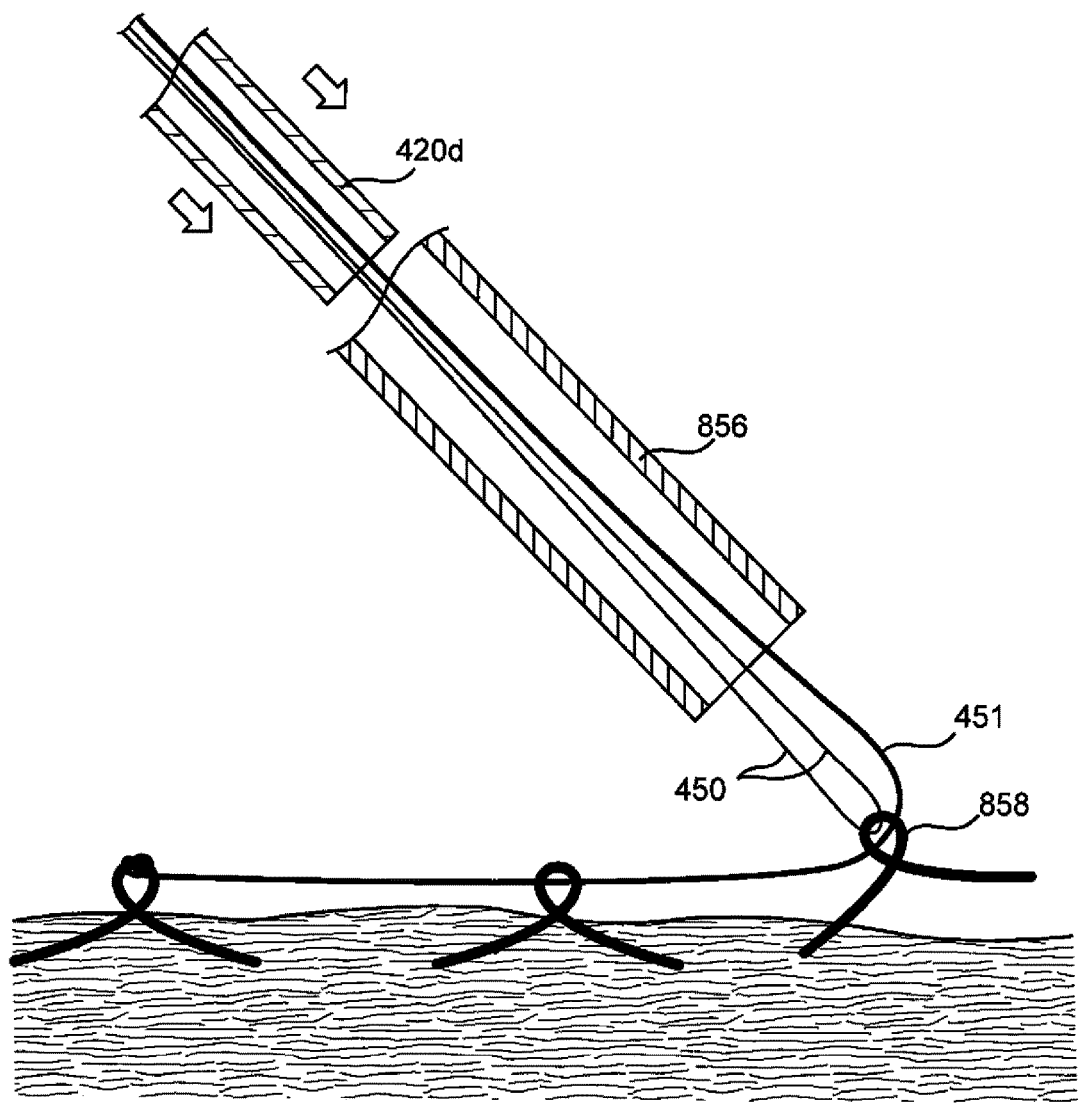
FIG. 8 depicts cross-sectional view of an implant retrieval device and a guide element.
Figure 9A:
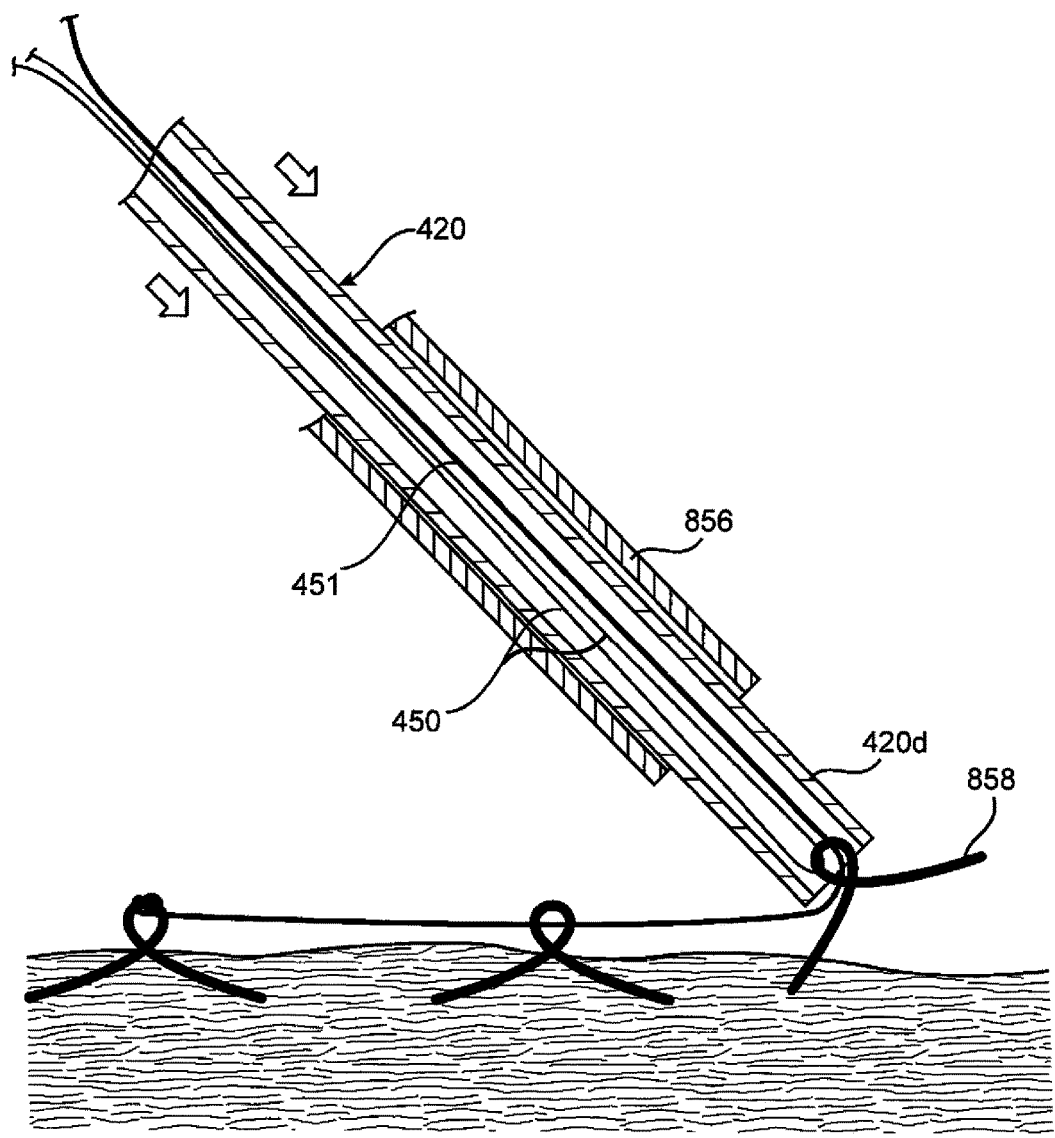
FIGS. 9A-9C depict cross-sectional views of the implant retrieval device and guide element in various configurations during use.

As depicted in FIG. 8, an outer elongate body of an implant retrieval device may optionally be advancing through a guide element, which may be a guide catheter, guide tunnel, and/or one or more tubular elongate members to abut or be in close proximity to, the implant or anchor. A guide element 856 may be positioned proximal to the implant or anchor 858 to be retrieved. While the anchor 858 is depicted as partially implanted within tissue, it should be understood that the anchor may be entirely implanted with the tissue, or may not be implanted in the tissue at all. While the outer elongate body is advanced, the inner elongate body may be held in place on the proximal end of the guide element 856 so that tension on the retrieval cable, retrieval tether and/or implant tether and stop or partition are maintained. Thus the inner elongate body may be held in a substantially stationary position while the outer elongate body is advanced toward the implanted and/or deployed device (e.g., anchor 858). Once the outer elongate body is positioned near the implant 858 to be removed, the outer elongate body 420 is no longer advanced (FIG. 9A). The inner elongate body may now be completely withdrawn from the outer elongate body, and the operator may release the tension on the retrieval cable. The retrieval tether 450 (and optionally the implant tether 451) may be unthreaded from the loop 425 of the inner elongate body retrieval cable. Where the implant tether 451 is a part of a tethered anchor assembly (e.g., for the treatment of heart valve regurgitation), the implant tether 451 may be separated from the retrieval tether 450 to ensure that the operator does not pull the implant tether as part of the anchor retrieval procedure. The operator may now manually, or with the assistance of some mechanical advantage (e.g., a motor), pull on the retrieval tether 450 (or wire hook) that is coupled to the anchor 858. By pulling on the retrieval tether, the anchor may be retrieved and drawn into the lumen of the outer elongate body. Although pulling the retrieval tether 450 may act to remove the proximal-most anchor 858 of a tethered anchor assembly, the tension of the implant tether 451 may not be affected, and none of the other anchors are removed from the tissue.

Figure 9B:
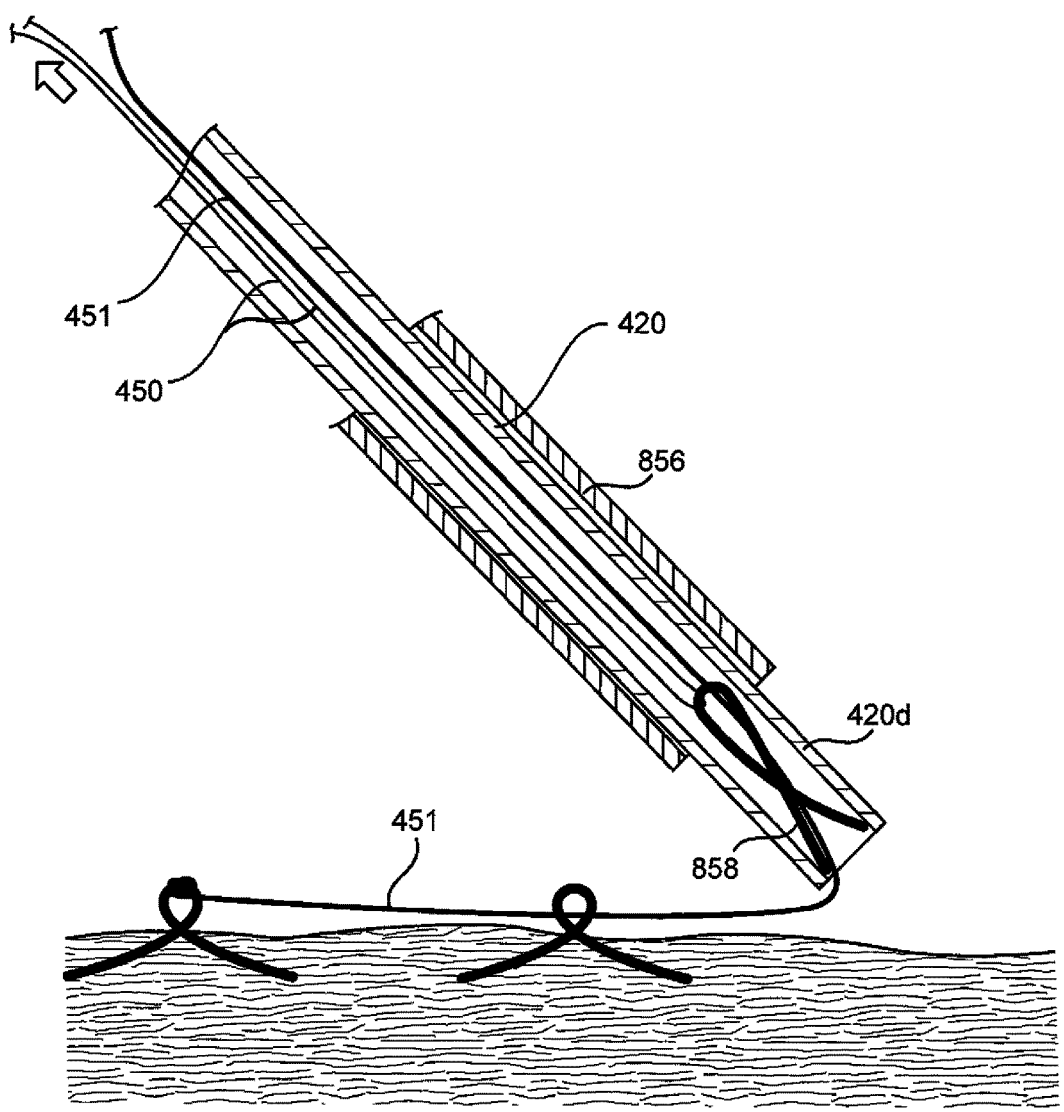
Figure 9C:
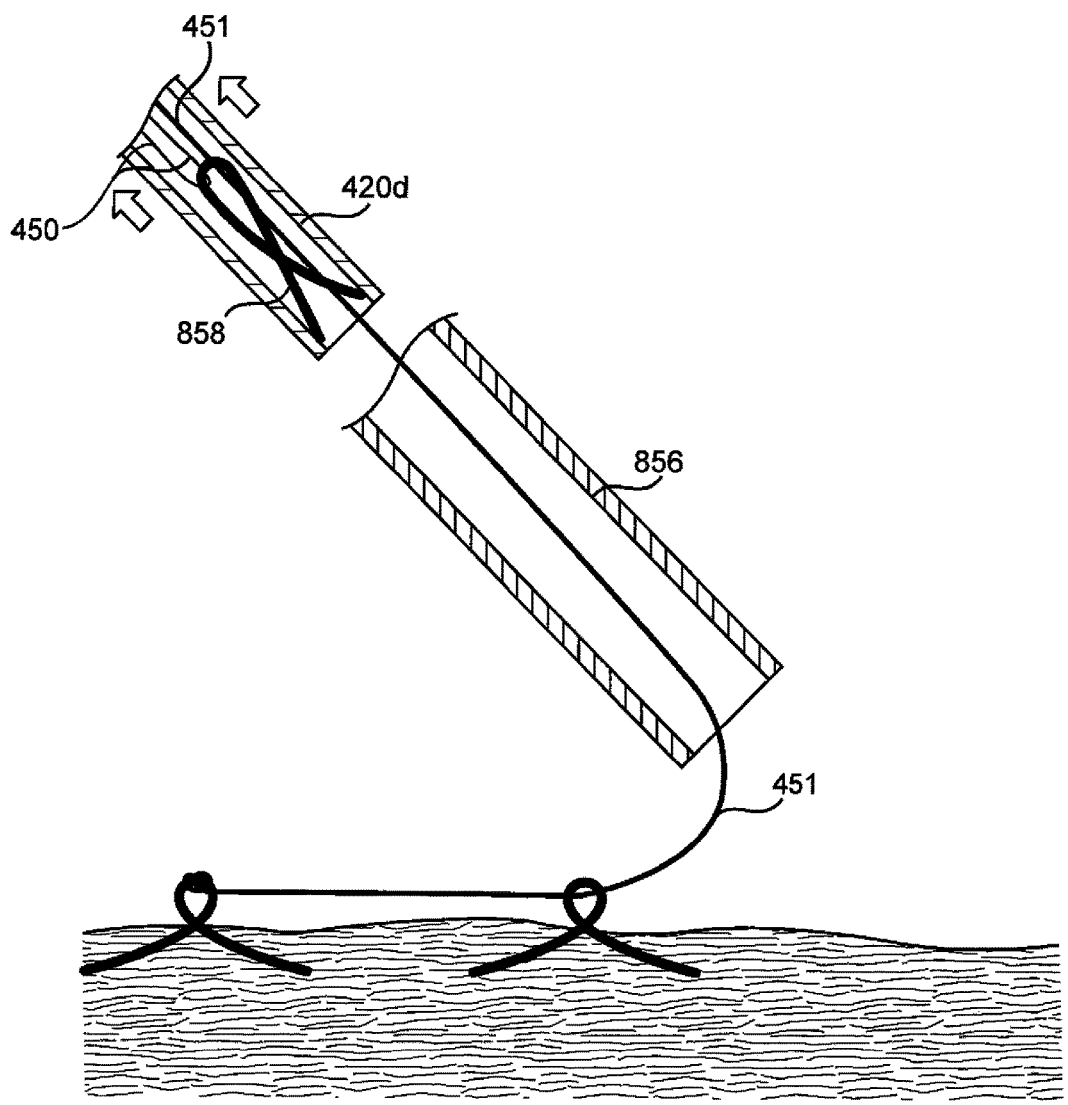

Once the implant or anchor 858 is pulled at least partially or entirely into the distal end 420*d* of the outer elongate body 420, as shown in FIG. 9B, the outer elongate body 420 may now be withdrawn proximally. The anchor may be retrieved and drawn into the outer elongate body 420 in any orientation or configuration, and may be retrieved into the outer elongate body in a different orientation or configuration from which it was deployed from the anchor delivery device. As described previously, the distal end of the outer elongate body may atraumatic, and may have an open lumen to ensure that the anchor may be readily withdrawn at least partially therein. The outer elongate body may be configured to retrieve an anchor regardless of its deployed and/or implanted configuration. In some variations, once the anchor has been retrieved into the lumen of the outer elongate body 420, the anchor may not be re-deployed. Once the outer elongate body 420 is withdrawn from the guide element 856, the implant tether 451 may remain coupled to the other anchors in the tethered-anchor assembly, and the deployment of additional anchors, a lock mechanism or additional retrievals may now be conducted (FIG. 9C). Alternatively or additionally, an implant retrieval device as described above may be used to cinch a tethered-anchor assembly by applying tension on the implant tether. This may help determine the amount of force necessary to attain the desired physiological state, which may expedite the final cinching and locking steps of the procedure (e.g., by reducing the amount imaging time, reducing the amount of imaging contrast injection, etc.).

Figure 10:
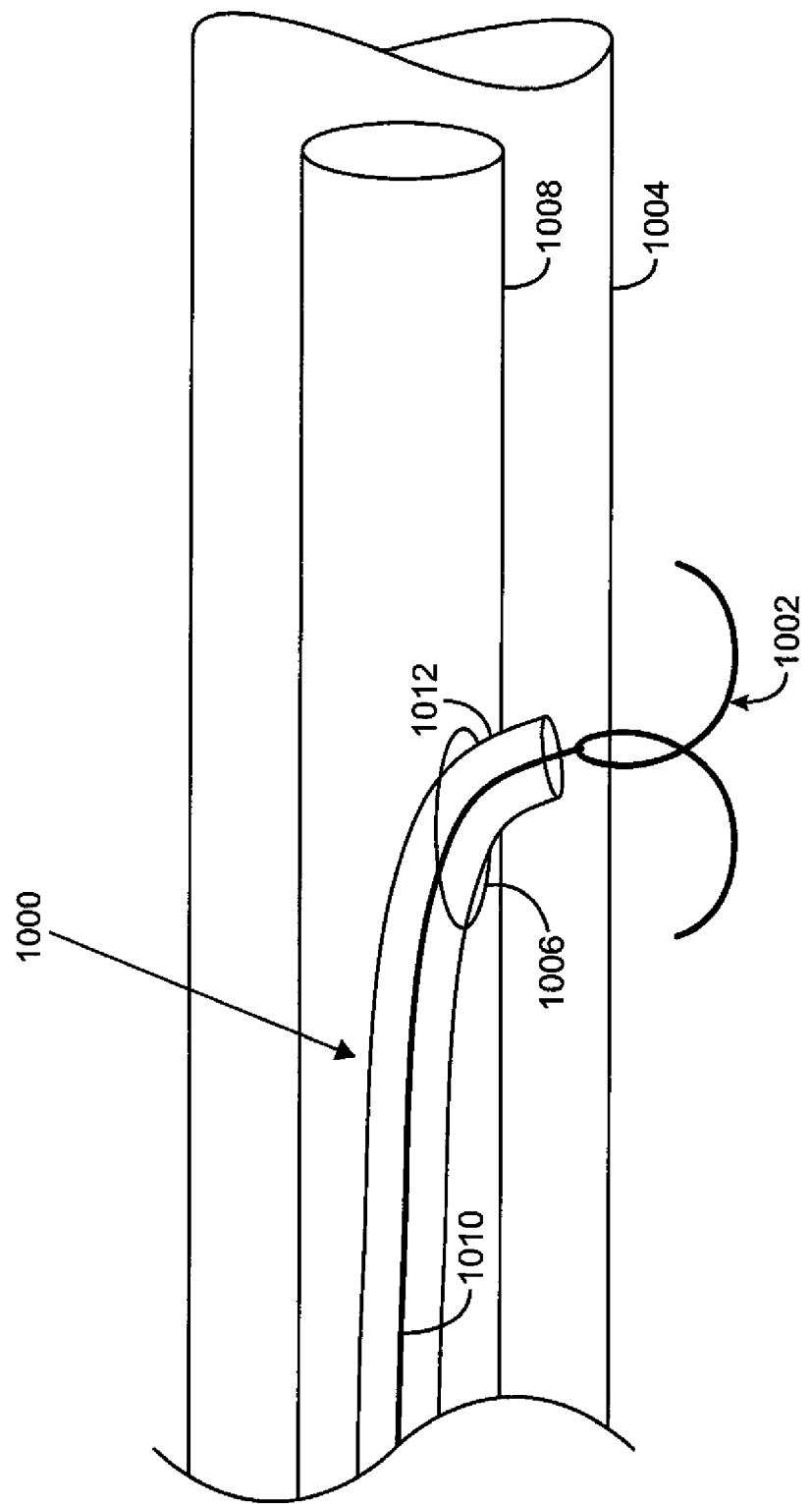
FIG. 10 depicts one variation of an implant retrieval system.

As described previously, a distal portion of the outer elongate body may have a pre-shaped curve. For example, as depicted in FIG. 10, an outer elongate body 1000 may have a curved distal region 1006, which may allow it to exit a side aperture 1012 of a guide element 1008 (e.g., a guide catheter or guide tunnel). In some variations, the guide catheter 1008 may be itself advanced through another second guide element 1004 (e.g., a second guide catheter or guide tunnel). The radius of curvature, angle (with respect to the proximal portion of the outer elongate body), stiffness or flexibility of the curved distal region 1006 may enable anchor to be consistently and reliably withdrawn into the lumen of the outer elongate body. The principles of the operation for capturing an implant or anchor remain the same as described above. Proximal withdrawal of the retrieval tether 1010 may pull the implant 1002 into the distal tip of the outer elongate body.

Figure 11A:
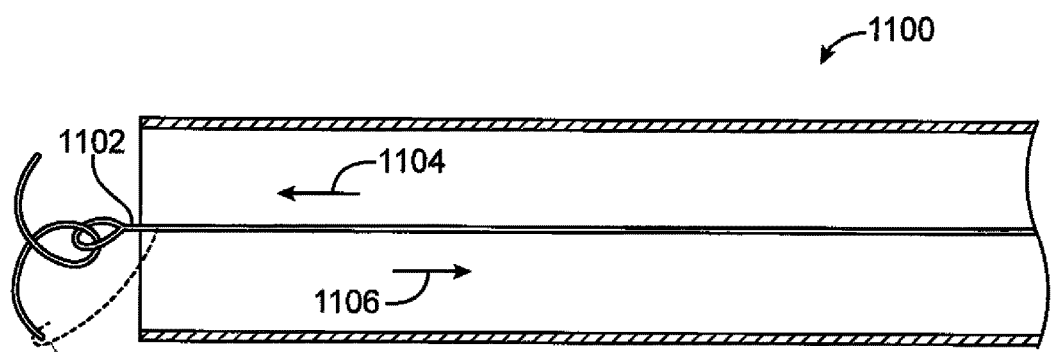
FIGS. 11A and 11B illustrate a capture of an implant using an implant deployment tool.
Figure 11B:
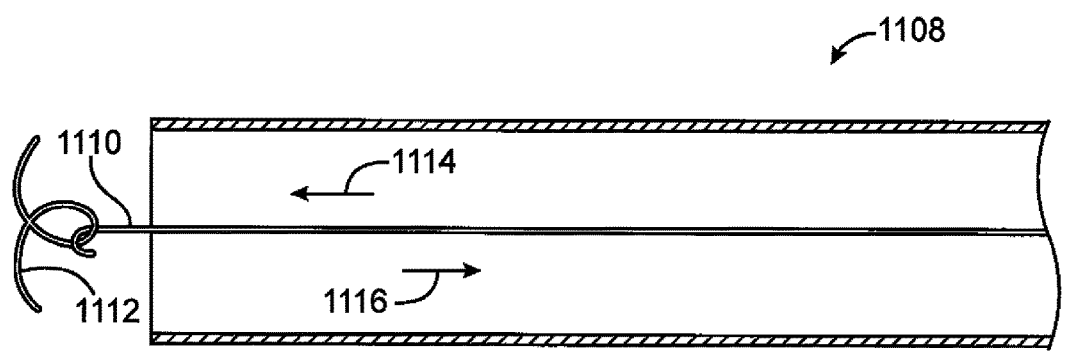

The implant retrieval devices described above may be capable of retrieving implants regardless of the orientation of the implant and without the possibility of re-deploying the implant (whether unintentionally or intentionally). In an another embodiment, the capture of a deployed implant may be achieved by using the same catheter or tool that was used to initially deploy the implant. As described above, some variations of methods and devices described here may be used to retrieve an anchor that has been incorrectly deployed (e.g., an anchor that has been deployed into a non-target site). For example, in certain variations, an anchor deployment catheter may be capable of retrieving an anchor. As an example, an anchor retrieval method may comprise compressing an anchor or anchors down to a collapsed configuration, and drawing the anchor or anchors back into a lumen of the shaft of the anchor delivery device. Any number of suitable devices or component parts may be useful in the retrieval process. For example, as shown in FIG. 11A-B, in some variations an anchor retrieval process may comprise coupling an anchor to a looped string or suture 1102 and loading the anchor into the anchor deployment catheter 1100. In this variation, the looped string 1102 is advanced distally 1104 out of catheter 1100, threaded onto one leg of the anchor (shown in FIG. 11A by dashed lines), and then slid around the anchor until it reaches, or is positioned about, the eyelet. Once looped string 1102 has been properly threaded, the anchor may be loaded into the anchor deployment catheter by pulling proximally 1106 on looped string 1102. Here, proximal pulling on the looped string can cause the anchor's legs to collapse against the anchor deployment catheter 1100, thereby allowing the anchor to be pulled therein. The looped string may also function to help with proper alignment and/or loading of the anchor into the anchor deployment catheter.

In another variation, shown in FIG. 11B, an anchor deployment catheter 1108 comprises a pull-push wire 1110. In a manner similar to that described with respect to FIG. 11A above, an anchor 1112 is first loaded or threaded onto push-pull wire 1110. This may be accomplished, for example, by pushing push-pull wire 1110 distally 1114 out of catheter 1108, and then loading anchor 1112 onto push-pull wire 1110 such that the distal hook of the push-pull wire 1110 is threaded through the eyelet of anchor 1112. The anchor may then be loaded into catheter 1108 by proximal pulling 1116 of push-pull wire 1110. As with the variation described above, the push-pull wire may also function to help with proper alignment and/or loading of the anchor into the anchor deployment catheter.

Figure 12A:
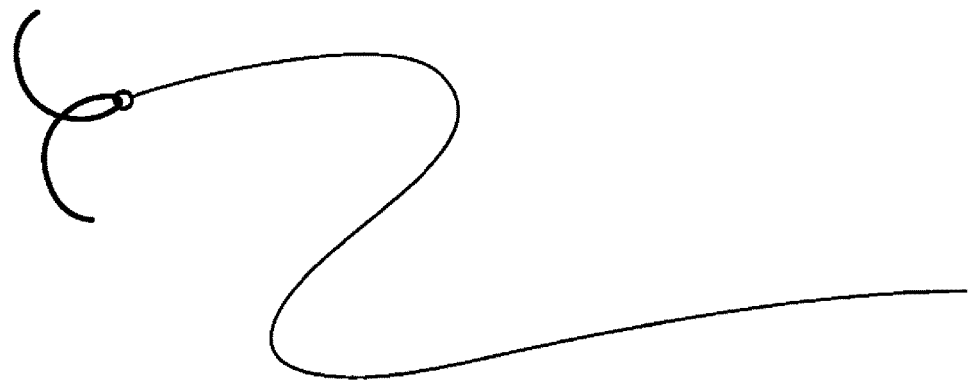
FIG. 12A-12C illustrate various embodiments of implants.
Figure 12B:
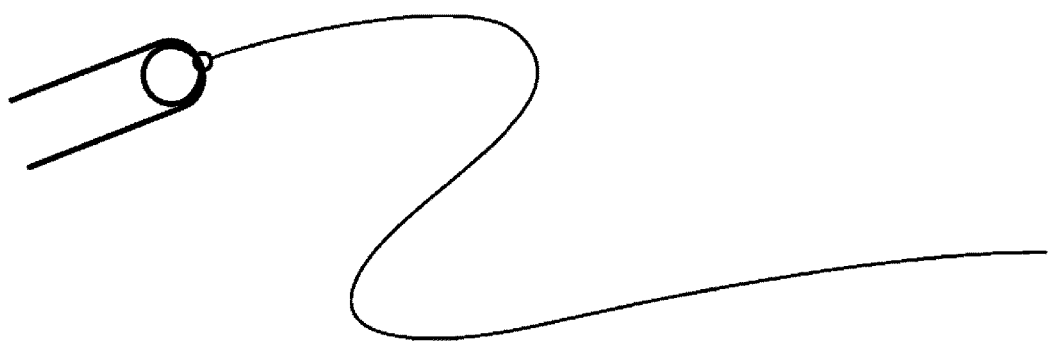
Figure 12C:
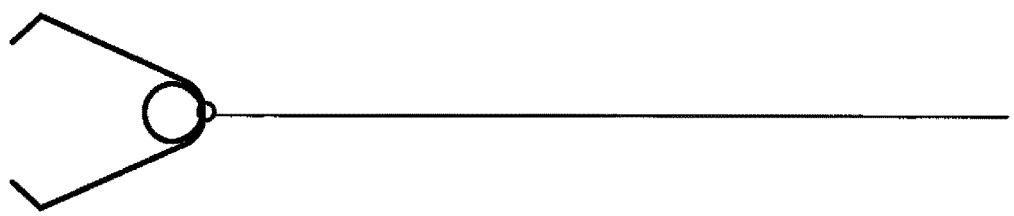

Various (non-limiting) embodiments of an implant or anchor attached or coupled to a retrieval tether are shown in FIGS. 12A-12C. While anchors are generally shown, the procedure and devices described herein are suitable for any implant that may have a retrieval tether attached to it, and where the implant may be safely taken up into the outer elongate body for recovery. The implant generally would not be reused, so the implant may suffer from plastic deformation without concern. The retrieval tether may be removably attached to the implant.

Figure 14:
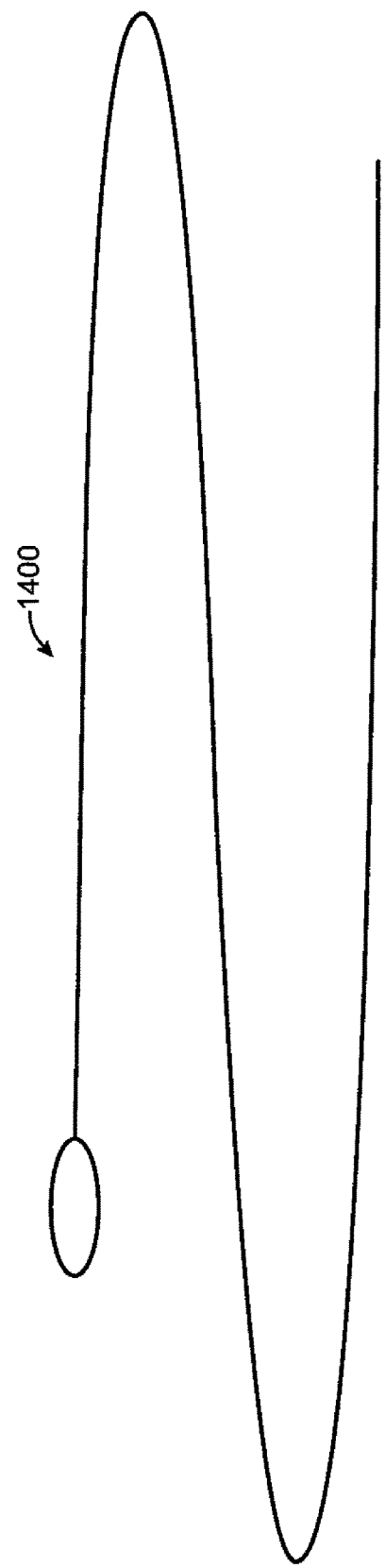
FIG. 14 illustrates an embodiment of a long snare.

Examples of two snares are now shown (FIGS. 13 and 14). A smaller, secondary snare 1300 may be used to help thread the loop of the larger snare 1400, especially when the larger loop is compressed or inaccessible due to placement in the inner elongate body. A tether (e.g., a retrieval tether, implant tether, etc.) may be threaded through the loop of the small snare, and then the small snare is threaded through the available loop of the larger snare. Once the tether(s) are threaded through the larger snare, the tether(s) may be removed from the smaller snare.

Operators of the devices and methods described herein may gain sufficient proficiency to operate a retrieval of an improved implant by "feel", or they may use a variety of well-known and widely used visualization devices to help determine the proper position and force of retrieving an implant.

The invention claimed is:

1. A retrievable implant assembly comprising:
    an anchor delivery catheter comprising a proximal end, a distal end, and a longitudinal lumen therebetween;
    an implantable tissue anchor disposed within the longitudinal lumen of the anchor delivery catheter, wherein the implantable tissue anchor comprises an eyelet;
    a tether coupled to the tissue anchor eyelet and extending through the longitudinal lumen of the anchor delivery catheter from the proximal end;
    an implant retrieval device comprising:
    an outer elongate body having a first longitudinal lumen extending therethrough;
    an inner elongate body configured to be slidably disposed within the first longitudinal lumen, wherein the inner elongate body comprises a second longitudinal lumen and a stop located within the second longitudinal lumen at a distal portion thereof;
    an actuator slidably coupled to the inner elongate body;
    a retrieval cable slidably disposed within the second longitudinal lumen of the inner elongate body and connected to the actuator such that the retrieval cable at least partially surrounds the stop to define a loop configured to capture the tether therein; and
    a retainer comprising a clamp disposed over the inner elongate body that locks the position of the actuator with respect to the inner elongate body such that the tether is restrained within the loop against the stop.

2. The assembly of claim 1, wherein the proximal ends of the retrieval cable are attached to the actuator.

3. The assembly of claim 1, wherein the outer elongate body has at least one radiopaque marker.

4. The assembly of claim 1, wherein the distal end of the outer elongate body is adapted to receive the implantable tissue anchor.

5. The assembly of claim 1, further comprising a motor configured to adjust the position of the actuator.

6. The assembly of claim 1, wherein the anchor delivery catheter is a first anchor delivery catheter and the implantable tissue anchor is a first implantable tissue anchor, and the assembly further comprises a second anchor delivery catheter and a second implantable tissue anchor comprising an eyelet disposed within the second anchor delivery catheter, wherein the tether is fixedly coupled to the eyelet of the first tissue anchor.

7. The assembly of claim 1, wherein the tether is 100 cm or greater in length.

8. The assembly of claim 1, wherein the position of the retrieval cable with respect to the stop varies according to the position of the actuator.

9. The assembly of claim 8, wherein the retrieval cable is constructed from a shape memory alloy.

10. The assembly of claim 8, wherein the inner elongate body has a first tether capturing configuration and a second tether locking configuration, wherein in the first configuration, the actuator is located in a distal position and in the second configuration, the actuator is located in a proximal position.

11. The assembly of claim 1, wherein the retainer comprises an O-ring.

12. The assembly of claim 11, wherein the retainer further comprises a sleeve proximal to the O-ring.

13. The assembly of claim 1, wherein the outer elongate body comprises a first pre-shaped curve with a first radius of curvature and a second pre-shaped curve located distal to the first pre-shaped curve, wherein the second pre-shaped curve has a second radius of curvature that is less than the first radius of curvature.

14. The assembly of claim 13, wherein the first radius of curvature is about 1.25 inches and the second radius of curvature is about 0.17 inch.

15. The assembly of claim 13, wherein the first radius of curvature is about 1.25 inches and the second radius of curvature is about 0.25 inch.

16. The assembly of claim 13, wherein the first pre-shaped curve comprises a material with a first durometer and the second pre-shaped curve comprises a material with a second durometer that is higher than the first durometer.

17. The assembly of claim 16, wherein the distal end of the outer elongate body has an atraumatic tip.

18. An implant retrieval device comprising:
    an outer elongate body;
    an inner elongate body slidably retained within the outer elongate body, wherein the inner elongate body comprises a first longitudinal lumen and a second longitudinal lumen, wherein the first and second longitudinal lumens are separated by a partition;
    a retrieval cable slidably disposed within the first and second longitudinal lumens, wherein the retrieval cable crosses between the first and second longitudinal lumens at a distal portion of the inner elongate body, wherein the retrieval cable crossing defines a loop;
    an actuator slidably coupled to the inner elongate body, wherein the proximal ends of the retrieval cable are attached to the actuator; and
    a retainer comprising a clamp disposed over the inner elongate body that locks the position of the actuator with respect to the inner elongate body.

19. A method of percutaneously retrieving a tissue anchor previously deployed into tissue within a patient body, the tissue anchor coupled to a tether extending from the deployed tissue anchor to outside the patient body, the method of retrieval comprising:
    providing an implant retrieval device comprising:
        an outer elongate body having a first longitudinal lumen extending therethrough,
        an inner elongate body slidably retained within the first longitudinal lumen, the inner elongate body comprising a second longitudinal lumen and a third longitudinal lumen, wherein the second and third longitudinal lumens are separated by a partition, an actuator slidably coupled to the inner elongate body, a retrieval cable slidably disposed within the second and third longitudinal lumens, wherein the retrieval cable crosses between the second and third longitudinal lumens at a distal portion of the inner elongate body such that the retrieval cable crossing defines a loop and wherein the retrieval cable is connected to the actuator, and a retainer comprising a clamp disposed over the inner elongate body that locks the position of the actuator with respect to the inner elongate body;

capturing the tether within the retrieval cable loop outside of the patient body;

locking the position of the actuator such that the tether is restrained within the loop;

withdrawing the inner elongate body with respect to the outer elongate body, thereby threading the tether through the outer elongate body;

advancing the outer elongate body within the patient body to the tissue anchor location;

applying proximally directed force on the tether to capture the tissue anchor within the outer elongate body; and withdrawing the outer elongate body from the patient, wherein the outer elongate body contains the anchor.

* * * * *